US011215845B2

(12) United States Patent
Schwarz et al.

(10) Patent No.: US 11,215,845 B2
(45) Date of Patent: Jan. 4, 2022

(54) METHOD, DEVICE, AND COMPUTER PROGRAM FOR VIRTUALLY ADJUSTING A SPECTACLE FRAME

(71) Applicant: Carl Zeiss Vision International GmbH, Aalen (DE)

(72) Inventors: Oliver Schwarz, Ellwangen (DE); Ivo Ihrke, Adelmannsfelden (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 16/699,590

(22) Filed: Nov. 30, 2019

(65) Prior Publication Data

US 2020/0103675 A1  Apr. 2, 2020

Related U.S. Application Data

(63) Continuation of application No. PCT/EP2018/064519, filed on Jun. 1, 2018.

(30) Foreign Application Priority Data

Jun. 1, 2017 (EP) .................................... 17173929

(51) Int. Cl.
*G02C 7/02* (2006.01)
*G02C 13/00* (2006.01)

(52) U.S. Cl.
CPC ............. *G02C 7/027* (2013.01); *G02C 7/028* (2013.01); *G02C 13/003* (2013.01)

(58) Field of Classification Search
CPC .... G02C 13/003; G02C 13/005; G02C 13/00; G02C 5/008; G02C 5/02; G02C 5/04;
(Continued)

(56) References Cited

U.S. PATENT DOCUMENTS 4,762,407 A    8/1988  Anger et al.
8,725,473 B2   5/2014  Clara
(Continued)

FOREIGN PATENT DOCUMENTS

CN    103456008 A    12/2013
CN    104408764 A    3/2015
(Continued)

OTHER PUBLICATIONS

Office action by the Chinese Patent Office issued in CN201880048493. 2, which is a counterpart hereof, dated Jun. 17, 2020, and English-language translation thereof.
(Continued)

*Primary Examiner* — Travis S Fissel
(74) *Attorney, Agent, or Firm* — Thrive IP®; Georg M. Hasselmann

(57) ABSTRACT

A virtual try-on process for spectacles includes an approximate positioning and a fine positioning of a spectacle frame on a head of a user. Provided for this purpose are 3D models of the head and the spectacle frame, as well as head metadata based on the model of the head and frame metadata based on the model of the frame. The head metadata contains placement information, in particular a placement point, which can be used for the approximate positioning of the spectacle frame on the head, and/or a placement region which describes a region of the earpiece part of the frame for placement on the ears of the head. A rapid and relatively simple computational positioning of the spectacle frame on the head and a more accurate positioning using a subsequent precise adjustment can be achieved with the aid of the metadata.

15 Claims, 9 Drawing Sheets

(58) Field of Classification Search
CPC ......... G02C 5/045; G06F 30/17; G06F 30/27; G16H 40/63; G16H 20/40; G16H 30/40; G06T 7/33; G06T 2207/30196; G06T 2219/2004; G06T 19/20; G06Q 30/0621; A61B 5/1079
USPC .............. 351/178, 124, 128, 136, 137, 158, 351/159.73–159.77
See application file for complete search history.

(56) References Cited

U.S. PATENT DOCUMENTS

| | | | |
|---|---|---|---|
| 9,286,715 | B2 | 3/2016 | Coon et al. |
| 9,304,332 | B2 | 4/2016 | Fonte et al. |
| 2002/0105530 | A1 | 8/2002 | Waupotitsch et al. |
| 2003/0123026 | A1 | 7/2003 | Abitbol et al. |
| 2003/0206178 | A1* | 11/2003 | Hoppe .................. G06T 17/205 345/582 |
| 2005/0162419 | A1 | 7/2005 | Kim et al. |
| 2006/0079757 | A1 | 4/2006 | Smith et al. |
| 2010/0022304 | A1 | 1/2010 | Katayama et al. |
| 2013/0088490 | A1 | 4/2013 | Rasmussen et al. |
| 2013/0321412 | A1 | 12/2013 | Coon et al. |
| 2015/0055085 | A1* | 2/2015 | Fonte .................. H04L 65/403 351/178 |
| 2016/0246078 | A1 | 8/2016 | Choukroun et al. |
| 2016/0284121 | A1 | 9/2016 | Azuma |
| 2016/0299360 | A1 | 10/2016 | Fonte et al. |
| 2016/0327811 | A1 | 11/2016 | Haddadi et al. |
| 2016/0360970 | A1 | 12/2016 | Tzvieli et al. |
| 2018/0096537 | A1* | 4/2018 | Kornilov ............ G06K 9/00228 |
| 2019/0037720 | A1 | 12/2019 | Fonte et al. |

FOREIGN PATENT DOCUMENTS

| | | |
|---|---|---|
| CN | 104881114 A | 9/2015 |
| CN | 104898832 A | 9/2015 |
| CN | 105842875 A | 8/2016 |
| DE | 10216824 A1 | 11/2003 |
| EP | 177638 A2 | 4/1986 |
| EP | 3355100 A1 | 8/2018 |
| EP | 3355102 A1 | 8/2018 |
| EP | 3355103 A1 | 8/2018 |
| ES | 2604806 A2 | 3/2017 |
| FR | 3016051 A1 | 7/2015 |
| FR | 3065295 A1 | 10/2018 |
| JP | 2012502306 A | 1/2012 |
| JP | 2016537716 A | 12/2016 |
| KR | 1020040097200 A | 11/2004 |
| KR | 1020160070744 A | 6/2016 |
| WO | 3188654 A2 | 11/2001 |
| WO | 03081536 A1 | 10/2003 |
| WO | 2010026220 A1 | 3/2010 |
| WO | 2013177456 A1 | 11/2013 |
| WO | 2015027196 A1 | 2/2015 |
| WO | 2015101738 A2 | 7/2015 |
| WO | 2016164859 A1 | 10/2016 |

OTHER PUBLICATIONS

Office action by the Japanese Patent Office issued in JP 2019-566300, which is a counterpart hereof, dated Jun. 30, 2020, and English-language translation thereof.
Hossein-Nejad et al.: "RKEM: Redundant Keypoint Elimination Method in Image Registration," IET Image Process., vol. 11 Iss. 5, pp. 273 to 284, 2017.
"Ophthalmic optics—Spectacle frames—Lists of equivalent terms and vocabulary," (ISO 7998:2005); German version EN ISO 7998:2005, Jan. 2006.
"Ophthalmic optics—Spectacle lenses—Vocabulary (ISO 13666:2012)," German and English version EN ISO 13666:2012, Oct. 2013.
"Ophthalmic optics—Spectacle frames—Measuring system and terminology," (ISO 8624:2011 + Amd.1:2015; German version EN ISO 8624:2011 + A1:2015), Dec. 2015.
"B-Spline," Wikipedia online encyclopedia entry [retrieved on Jan. 31, 2020], retrieved from the Internet using <URL: en.wikipedia.org/w/index.php?title=B-spline&oldid=8407870478U >, last edited Dec. 18, 2019.
"Bildsynthese [Rendering]," Wikipedia online encyclopedia entry [retrieved on Jan. 31, 2020], and English-language counterpart entry thereof, retrieved from the Internet using <URL: de.wikipedia.org/wiki/Bildsynthese>, last edited Dec. 30, 2019.
Breiman "Random forests," Machine learning 45.1, (2001).
Cignoni et al. "Meshlab: an open-source mesh processing tool," Eurographics Italian Chapter Conference, 2008.
"cv::ml::RTrees," Open CV software library, retrieved from the Internet using <URL: docs.opencv.org/3.1.0/d0/d65/classcv_1_1ml_1_1RTrees.html, last accessed Jan. 31, 2020.
De Boor et al. "A practical guide to splines," vol. 27, Chapter XVII, New York: Springer-Verlag, 1978.
Demonstration video for "Vacker" software by VOLUMENTAL (two screenshots), available at the url: "www.volumental.com/face-scanning/," last accessed Mar. 5, 2017.
"Fast point feature histograms (FPFH) descriptors," retrieved from the Internet using <URL: pointclouds.org/documentation/tutorials/fpfh_estimation.php>, last accessed Jan. 31, 2020.
"Frontalebene [Coronal plane]," Wikipedia online encyclopedia entry [retrieved on Jan. 31, 2020], and English-language counterpart entry thereof, retrieved from the Internet using <URL: de.wikipedia.org/wiki/Hauptkomponentenanalyse>, last edited May 18, 2018.
Hartley et al.,: "Multiple View Geometry in Computer Vision," 2nd edition, pp. 1 to 8, Cambridge University Press 2004.
"Hauptkomponentenanalyse [principal component analysis]," Wikipedia online encyclopedia entry [retrieved on Jan. 31, 2020], and English-language counterpart entry thereof, retrieved from the Internet using <URL: de.wikipedia.org/wiki/Hauptkomponentenanalyse>, last edited Sep. 29, 2019.
"Hauptkrümmung [principle curvature]," Wikipedia online encyclopedia entry [retrieved on Jan. 31, 2020], and English-language counterpart entry thereof, retrieved from the Internet using <URL: de.wikipedia.org/wiki/Hauptkr%C3%BCmmung>, last edited Jan. 26, 2020.
Hirschmüller et al.: "Stereo Processing by Semiglobal Matching and Mutual Information," in IEEE Transactions on Pattern Analysis and Machine Intelligence, vol. 30, No. 2, pp. 328-341, doi: 10.1109/TPAMI.2007.1166, Feb. 2008.
Kazemi et al. "One Millisecond Face Alignment with an Ensemble of Regression Trees," IEEE Conference on Computer Vision and Pattern Recognition, 2014.
"Körper (Geometrie) [Body (Geometry)]," Wikipedia online encyclopedia entry [retrieved on Jan. 31, 2020], and English-language machine translation thereof, retrieved from the Internet using <URL: de.wikipedia.org/w/index.php?title=K%C3%B6rper_(Geometrie)&oldid=177672595>, last edited Dec. 20, 2019.
"Legendre-Polynom [Legendre-polynomials]," Wikipedia online encyclopedia entry [retrieved on Jan. 31, 2020], and English-language counterpart entry thereof, retrieved from the Internet using <URL: de.wikipedia.org/wiki/Legendre-Polynom >, last edited Jan. 3, 2020.
"L'essayage virtuel par DITTO [Virtual tryon by DITTO]," eight screenshots from Alain Afflelou/Ditto youtube presentation [retrieved on Jan. 30, 2020], retrieved from the Internet using <URL: www.youtube.com/watch?v=ZsBV4FkcU8U > posted Jun. 18, 2015.
"Machine Learning Overview," Open Source Computer Vision, retrieved from the Internet using <URL: Docs.opencv.org//3.1.0/dc/dd6/ml_intro.html, last accessed Jan. 31, 2020.
"Maschinelles Lernen [Machine Learning]," Wikipedia online encyclopedia entry [retrieved on Jan. 31, 2020], and English-language counterpart entry thereof, retrieved from the Internet using <URL: de.wikipedia.org/wiki/Maschinelles_Lernen>, last edited Jan. 26, 2020.
"Metadaten [Metadata]," Wikipedia online encyclopedia entry [retrieved on Jan. 31, 2020], and English-language counterpart entry thereof, retrieved from the Internet using <URL: de.wikipedia.org/wiki/Metadaten>, last edited Jan. 1, 2020.
Niessner et al. "Real-time 3D reconstruction at scale using voxel hashing," ACM Trans. Graph. 32, 6, Article 169, available at the url doi.org/10.1145/2508363.2508374, Nov. 2013.

(56) References Cited

OTHER PUBLICATIONS

Rau et al. "A Semi-Automatic Image-Based Close Range 3D Modeling Pipeline Using a Multi-Camera Configuration," Sensors (Basel, Switzerland), 2012;12(8), pp. 11271 to 11293, doi:10.3390/s120811271, Aug. 14, 2012.

"Ray Tracing," Wikipedia online encyclopedia entry [retrieved on Jan. 31, 2020], retrieved from the Internet using <URL: en.wikipedia org/wiki/Ray_tracing_(graphics) >, last edited Jan. 29, 2020.

"Real-time face pose estimation," retrieved from the Internet using <URL: blog.dlib.net/2014/08/real-time-face-pose-estimation.html, as of Mar. 10, 2017, last accessed Jan. 31, 2020.

RUSU "Semantic 3D Object Maps for Everyday Manipulation in Human Living Environments," Dissertation, TU Munich, 2009.

Salti et al. "Learning a Descriptor-specific 3D Keypoint Detector," Proceedings of the 2015 IEEE International Conference on Computer Vision (ICCV) (ICCV '15). IEEE Computer Society, Washington, DC, USA, 2318-2326, available at the url dx.doi.org/10.1109/ICCV.2015.267, last accessed Jan. 31, 2020.

"Support vector machine (SVM)", Open CV software library, retrieved from the Internet using <URL: docs.opencv.org/master/d1/d2d/classcv_1_1ml_1_1SVM.html, last accessed Jan. 31, 2020.

"Transversalebene [Transverse plane]," Wikipedia online encyclopedia entry [retrieved on Jan. 31, 2020], and English-language counterpart entry thereof, retrieved from the Internet using <URL: de.wikipedia.org/wiki/Transversalebene>, last edited Jan. 8, 2019.

"Überwachtes Lernen [Supervised learning]," Wikipedia online encyclopedia entry [retrieved on Jan. 31, 2020], and English-language counterpart entry thereof, retrieved from the Internet using <URL: de.wikipedia.org/wiki/Legendre-Polynom >, last edited Nov. 29, 2019.

Virtual spectacle fitting, eight screenshots from Alain Afflelou/Ditto youtube presentation [retrieved on Jan. 30, 2020], retrieved from the Internet using <URL: www.youtube.com/watch?v=awNs2cEoZ7Y>, posted Jun. 18, 2015.

Zhu et al. "Face detection, pose estimation and landmark localization in the wild," CVPR 2012, and presentation of the article on homepage of the first author, 2013.

International Search Report and English-language translation thereof issued in PCT/EP2018/064519, which is a counterpart hereof, dated Oct. 9, 2018.

Written opinion issued in PCT/EP2018/064519, which is a counterpart hereof, dated Dec. 7, 2018.

International Preliminary Report on Patentability issued in PCT/EP2018/064519, which is a counterpart hereof, completed Sep. 9, 2019.

Office action by the Canadian Patent Office issued in CA3,082,642, which is a counterpart application hereof, dated Jul. 14, 2021.

\* cited by examiner

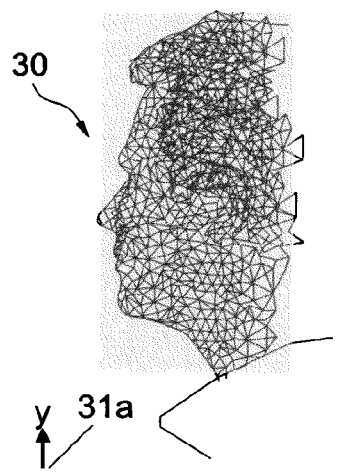
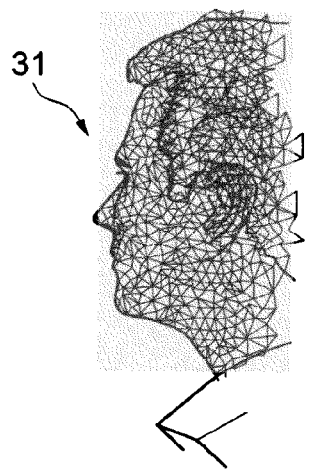
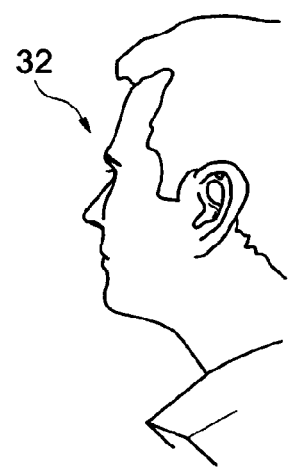
FIG. 3A  FIG. 3B  FIG. 3C
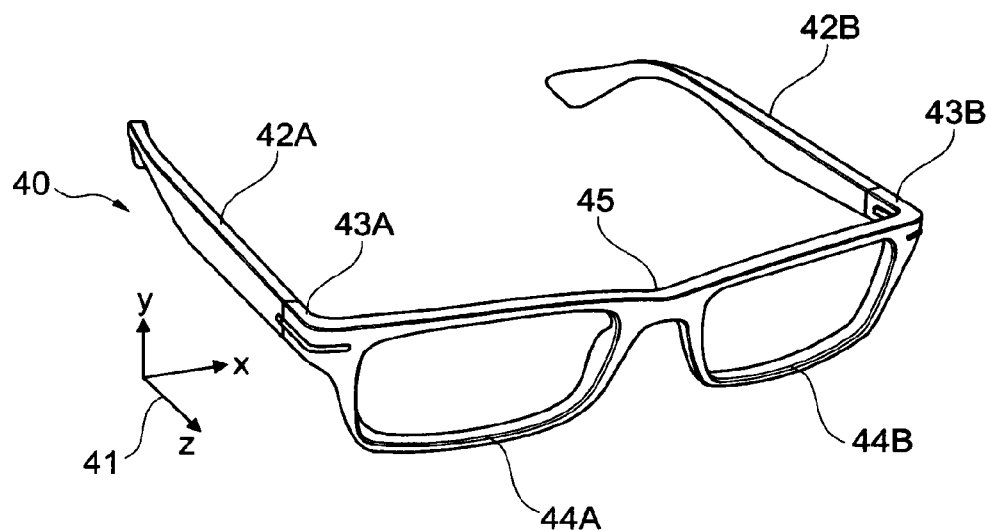
FIG. 4

METHOD, DEVICE, AND COMPUTER PROGRAM FOR VIRTUALLY ADJUSTING A SPECTACLE FRAME

CROSS REFERENCE TO RELATED APPLICATIONS

This application is a continuation application of international application PCT/EP2018/064519, filed Jun. 1, 2018, which claims priority to European patent application EP 17173929.5, filed Jun. 1, 2017, both of which are hereby incorporated by reference in their entireties.

TECHNICAL FIELD

The present application relates to methods, apparatuses, and computer programs for virtual fitting of spectacle frames. Here, pursuant to DIN EN ISO 7998:2006-01 and DIN EN ISO 8624:2015-12, a spectacle frame should be understood to mean a frame or a holder by means of which spectacle lenses can be worn on the head. In particular, the term as used herein also contains rimless spectacle frames. Colloquially, said spectacle frames are also referred to as frames. Within the scope of the present application, virtual donning of a spectacle frame denotes fitting a model of a spectacle frame to a model of a head on a computing device, usually connected with a graphical representation of the fitting of the spectacle frame to a head of a person on a display, for example a computer monitor.

BACKGROUND

Virtual donning of a spectacle frame is known from US 2003/0123026 A1 or US 2002/0105530 A1, for example. In these documents, virtual donning of the spectacle frame predominantly serves to help a user to choose between different spectacle frames by virtue of a graphic representation of the head of the user being displayed together with the spectacle frame.

WO 2015/101738 A2, corresponding to US 2016/0327811 A1, discloses a method for virtual fitting of a spectacle frame to a user. Here, a model of the head of the user, in particular a model of the nose and a model of the two ears of the user, is used. A superposition of a model of the spectacle frame on the model of the head is used to determine a necessary deformation of the spectacle frame by virtue of an overlapping region being minimized such that the spectacle frame fits on the head of the user. This deformation can be applied to the corresponding real spectacle frame, either by way of a machine or else by hand. Additionally, a position of the frame in relation to the nose can be automatically optimized in this document. This optimization requires relatively high computational outlay and, depending on the initial values of the optimization, ideal fitting is not, in fact, necessarily ensured.

U.S. Pat. No. 9,286,715 B2 discloses a method for a virtual try-on of a pair of spectacles. Here, a plurality of points are defined, both in the spectacle frame and on a head. The spectacle frame is positioned on the head by virtue of selected points on the spectacle frame being brought into correspondence with selected points on the head. A position is changed by changing the selected points. This facilitates positioning with an accuracy that is sufficient for the purpose of U.S. Pat. No. 9,286,715 B2 of obtaining a virtual try-on for the purposes of obtaining a visual impression. Accurate fitting, on the basis of which an optician can then undertake real fitting of a frame, is not achieved in this case.

VOLUMENTAL has made available a demonstration video for "Vacker" software at the url "www.volumental.com/face-scanning/", as of Mar. 5, 2017, in which a head with a donned pair of spectacles is presented and parameters of the pair of spectacles are modifiable by means of sliders, for example the seat of the pair of spectacles on the nasal bridge, or else other parameters such as face form angle and "as-worn" pantoscopic angle (cf., DIN EN ISO). A color of the spectacle frame or a color of the hinge of the spectacle frame can also be selected.

Videos showing the workflow of virtual spectacle fitting are available on the Youtube web portal of Alain Afflelou/Ditto. See, for example, the videos available at www.youtube.com/watch?v=awNs2cEoZ7Y, as of Mar. 5, 2017 or www.youtube.com/watch?v=ZsBV4FkcU8U, also as of Mar. 5, 2017. Here, a computer with an integrated camera is used as a recording system and frames can be selected. In this procedure, a pair of spectacles is fitted, as it were, on a live video of the user, which is recorded with the camera.

The related art explained above allows virtual donning of a pair of spectacles and, e.g., in the case of WO 2015/101738 A2, even a certain degree of fitting of the pair of spectacles to the user so as then to transfer this fitting to a real spectacle frame such that a pair of spectacles with the spectacle frame can subsequently be provided directly for the user with as little further fitting as possible. As explained, the method in WO 2015/101738 A2 requires comparatively high computational outlay, however, as an optimization is carried out on the basis of the superposition of 3D models. Moreover, it remains uncertain in the optimization method of this document as to whether an optimum is in fact found or whether the optimization method "remains stuck" in, e.g., a local minimum of a quantity to be optimized.

FR 301 6051 A1 discloses a computer-implemented method for virtual fitting of a pair of spectacles.

US 2013/0088490 A1 discloses a computer-implemented method for virtual fitting of a pair of spectacles.

ES 260 4806 A2 discloses a method for determining parameters for glasses of spectacle frames and for ordering lenses determined thus. The described methods comprise: obtaining morphological data of the head of the user, determining the optimal position of the lenses, determining the possible spectacle frames from the spectacle frames of a spectacle frame database and excluding spectacle frames that are not possible, calculating a possible pair of lenses for each possible spectacle frame and excluding spectacle frames without usable lenses, selecting at least one realizable spectacle frame from a database of realizable glasses by a user, confirming a selection, and placing an order.

WO 01/88654 A2 discloses a spectacle fitting system comprising an imaging system that facilitates a view of the face of the customer, a 3D image processor for generating first 3D information items that describe the physical features of the customer, a virtual try-on unit for receiving the digital 3D representation of the face of the customer and a digital 3D representation of a spectacle frame in order to virtually place the spectacle frame onto the face of the customer and generate a second 3D information item that describes the frame/face fit and a lens fitter that is configured to receive the first 3D information items and the second 3D information item and generate at least one parameter therefrom for the customer-specific face and frame production and for grinding the lens. In this context, WO 01/88654 A2 discloses an automatic assignment of facial features by means of a "3D face extractor" and the manual determination of head metadata by means of manual measurements.

WO 2016/0164859 A1 discloses systems and methods for producing a spectacle frame and lens geometry, which is fitted to the anatomy of a user and optimized for the refractive index of the user. A method comprises: receiving a configurable parametric model of a user-specific spectacle product comprising a frame part and a lens part, wherein geometric parameters of the configurable parametric model are based on geometric features of the anatomy of a user; receiving media data of a user, wherein the media data contain the reaction of the user to visual cues; detecting the position of the eyes of the user from the received media data; determining the optical information item of the user on the basis of the identified position of the eyes of the user; and generating an updated configurable parametric model by modifying the received configurable parametric model on the basis of the determined optical information item. In this context, WO 2016/0164859 A1 discloses the use of machine learning for detecting facial features and the calculation of information items for the illumination in recordings of a head and the virtual representation of spectacle frames with an appropriately adapted virtual illumination.

Using the method described in FR 301 6051 A1, it is possible to virtually don a spectacle frame, wherein the spectacle frame is positioned on the head of the user by means of approximate positioning and fine positioning.

SUMMARY

It is an object of the present disclosure to provide a method that makes the fine virtual positioning faster, easier, and more reliable. For this purpose, according to a first aspect of the disclosure, a computer-implemented method for virtual fitting of a pair of spectacles is provided.

It is another object of the present application to reduce the computational demands for carrying out the method. For this purpose, according to another aspect of the disclosure, an approximate virtual positioning of a spectacle frame on a head on the basis of head metadata for a 3D model of the head and frame metadata for a 3D model of the spectacle frame is performed before the fine virtual positioning.

US 2013/0088490 A1 discloses a segmentation of the 3D model of the spectacle frame into components of the spectacle frame. Proceeding from US 2013/0088490 A1, it is yet another object of the present application to make the segmentation more easily implementable from a computational point of view. For this purpose, an approximate virtual positioning of the spectacle frame on the head on the basis of head metadata for the 3D model of the head and frame metadata for the 3D model of the spectacle frame is performed before the fine virtual positioning.

Proceeding from US 2013/0088490 A1, it is a further object of the present application to make a determination of the resting region for the ears of the head more easily implementable from a computational point of view. For this purpose, an approximate virtual positioning of the spectacle frame on the head on the basis of head metadata includes resting regions for the ears of the head is provided.

Likewise proceeding from FR 301 6051 A1, it is another object of the present application to improve the information item characterizing the nasal bridge of the head to improve the accuracy of the spectacle fitting method and simultaneously reduce the memory requirements of the method. For this purpose, an approximate virtual positioning of the spectacle frame on the head on the basis of head metadata includes resting information concerning a placement point associated with a nasal bridge of the 3D model of the head.

Further exemplary embodiments are discussed in detail below.

Likewise, computer programs for implementing the methods herein are provided for all aspects of the disclosure.

The disclosure is discussed briefly below. The employed terminology is defined following this brief discussion.

In an aspect of the disclosure, a computer-implemented method for virtual fitting of a pair of spectacles is provided, the method comprising:

approximate virtual positioning of a spectacle frame on a head on the basis of head metadata for a 3D model (30, 31) of the head and frame metadata for a 3D model of the spectacle frame, and subsequent fine virtual positioning of the spectacle frame on the basis of the 3D model (30, 31) of the head and the 3D model (40) of the spectacle frame.

It would be possible here, for example, for the approximate virtual positioning to determine an initial position and orientation of the spectacle frame for the fine virtual positioning, wherein the fine virtual positioning can be implemented proceeding from the initial position and orientation.

The method includes that if a horizontal direction corresponding to a connecting line between pupil centers of eyes of the head in a main fixation direction is defined as x-direction when the head is held erect, and if a vertical direction when the head is held erect is defined as y-direction and if a direction perpendicular to the x-direction and to the y-direction is defined as z-direction then, during the fine virtual positioning, there is a first displacement of the spectacle frame by a first distance perpendicular to the z-direction, and there is a second displacement of the spectacle frame by a second distance along the z-direction, wherein the second distance is no more than 10% of the first distance.

Compared to the method of FR 301 6051 A1, such a method is advantageous in that it makes the fine virtual positioning faster, easier, and more reliable by virtue of substantially restricting the fine positioning to positioning in a plane (the xy-plane, i.e., perpendicular to the z-direction) and consequently restricting the degrees of freedom during the fine positioning.

In the second aspect of the disclosure, a computer-implemented method for virtual fitting of a pair of spectacles is provided, comprising:

approximate virtual positioning of a spectacle frame on a head on the basis of head metadata for a 3D model (30, 31) of the head and frame metadata for a 3D model of the spectacle frame before the fine virtual positioning, and fine virtual positioning of the spectacle frame on the basis of the 3D model (30, 31) of the head and the 3D model (40) of the spectacle frame, wherein the method for providing the frame metadata comprises identifying prominent points in the 3D model of the spectacle frame and/or classifying prominent points in the 3D model of the spectacle frame.

The method includes classifying prominent points into relevant and non-relevant points.

Compared to the method of FR 301 6051 A1, such a method is advantageous in that the computational demands for carrying out the method are reduced since only a subset of the determined points, specifically the relevant points, are taken into account when the method is carried out.

In the third aspect of the disclosure, a computer-implemented method for virtual fitting of a pair of spectacles is provided, comprising:

fine virtual positioning of a spectacle frame on the basis of a 3D model (30, 31) of a head and a 3D model (40) of the spectacle frame, approximate virtual positioning of the spectacle frame on the head on the basis of head metadata for the 3D model (30, 31) of the head and frame metadata for the 3D model of the spectacle frame before the fine virtual positioning, wherein the provision of the frame metadata comprises a segmentation of the 3D model of the spectacle frame into components of the spectacle frame, wherein the components preferably comprise at least one component of the group earpiece parts a remaining part of the spectacle frame apart from earpiece parts and/or wherein the head metadata comprise resting regions for the ears of the head, which regions are calculated on the basis of the earpiece parts.

The method is characterized in that the segmentation of the 3D model of the spectacle frame into components of the spectacle frame is implemented by means of respective sectional planes in space, which subdivide vertices or voxels of the 3D model, wherein the respective sectional planes are defined by a respective reference point p and a respective normal vector n, which is perpendicular to the respective sectional plane in space, and wherein the segmentation of the 3D model of the spectacle frame is implemented on the basis of a comparison of the scalar product of a vertex or voxel of the 3D model of the spectacle frame with the respective normal vector n with a scalar product of the respective reference point p with the normal vector n.

Compared to the method for segmenting the 3D model of the spectacle frame into components of the spectacle frame known from US 2013/0088490 A1, the method according to the third aspect of the disclosure is advantageous in that the segmentation is provided in a computationally easily implementable manner.

According to the fourth aspect of the disclosure, a computer-implemented method for virtual fitting of a pair of spectacles is provided, comprising:

fine virtual positioning of a spectacle frame on the basis of a 3D model (30, 31) of the head and a 3D model (40) of the spectacle frame, approximate virtual positioning of the spectacle frame on the head on the basis of head metadata for the 3D model (30, 31) of the head and frame metadata for the 3D model of the spectacle frame before the fine virtual positioning, wherein the provision of the frame metadata comprises a segmentation of the 3D model of the spectacle frame into components of the spectacle frame, wherein the components preferably comprise at least one component of the group earpiece parts a remaining part of the spectacle frame apart from earpiece parts and wherein the head metadata comprise resting regions for the ears of the head, which regions are calculated on the basis of the earpiece parts.

The method includes determining at least one resting region of the calculated resting regions for the ears of the head for at least one spectacle earpiece of the earpiece parts, wherein the method further includes:

determining a start point a and an endpoint b of the spectacle earpiece from the spectacle earpiece, determining a potential ear resting region by way of z-components of planes that delimit the potential ear resting region, wherein the following applies:

$$\alpha < (v_z - a_z)/l_z < \beta,$$

where $\alpha$ and $\beta$ are predetermined values, where $\alpha$ lies between 0.3 and 0.6 and $\beta$ lies between 0.6 and 0.9 and where $a_z$ is the z-component of the point a and $l_z$ is the length of the spectacle earpiece in the z-direction and where $v_z$ is the z-component of a vertex or voxel of the 3D model, determining the resting region from the potential ear resting region by way of a calculation with an incrementally displaced window, where the set of vertices or voxels of the potential resting region lying in the window is ascertained for each position of the window and the scalar product $s = \langle v, d \rangle$ with a direction vector d is formed for each of the sets of vertices or voxels, where v specifies the coordinates of the respective vertex or voxel from the set of vertices or voxels, where d is a normalized fixed vector for the respective spectacle earpiece and respectively one vertex or voxel $\hat{v}$ is determined for the respective window on the basis of the scalar products s of the vertices or voxels, and providing the at least one resting region as a set of resting points or as a resting curve, wherein the set of resting points or resting curve comprises the vertices or voxels v.

Compared to the method known from US 2013/0088490 A1, the method according to the fourth aspect of the disclosure is advantageous in that determining the resting region for the ears of the head is provided in a computationally easily implementable manner.

According to the fifth aspect of the disclosure, a computer-implemented method for virtual fitting of a pair of spectacles is provided, comprising:

virtual positioning of a spectacle frame on a head on the basis of head metadata for a 3D model (30, 31) of the head and frame metadata for a 3D model of the spectacle frame, wherein the frame metadata comprise first resting information items, which define one or more locations on the spectacle frame where the spectacle frame rests on the head, and the head metadata comprise second resting information items, which define one or more locations on the head where the spectacle frame rests on the head, and wherein the second resting information items comprise a placement point associated with a nasal bridge of the 3D model of the head.

The method is characterized in that a nasal bridge region of the nasal bridge is provided as a 3D curve.

Compared to the method of FR 301 6051 A1, this is advantageous in that the computational requirements for carrying out the method are reduced since no collision point calculation with a three-dimensional mesh, i.e., a full three-dimensional model, is required; instead, approximate positioning can be determined by determining a point only using a curve. At the same time, the accuracy of the spectacle fitting method is improved since a 3D curve is suitable for describing the contour of the nose using less data than a mesh, while having a greater accuracy.

Approximate positioning is understood to mean that an initial position is determined on the basis of information items. Fine positioning is understood to mean that, proceeding from approximate positioning, a more accurate determination of position is carried out on the basis of further data. By way of example, positioning could be carried out along the z-direction within the scope of approximate positioning; and positioning could subsequently be implemented substantially perpendicular to the z-direction within the scope of the fine positioning.

Here, approximate positioning can be implemented on the basis information items about the nasal bridge: Here, a 3D point in the coordinate system of the frame, which is also referred to as an anchoring point, can be made congruent with a point on the nasal bridge.

In some exemplary embodiments, the fine positioning can move the spectacle frame by less than 20 mm, in some exemplary embodiments by less than 10 mm, in relation to the initial position and orientation, i.e., the position of the spectacle frame determined by the approximate positioning.

Here, the terms "approximate positioning" and "fine positioning" should be understood relative to one another; i.e., fine positioning makes the position initially determined during approximate positioning more precise.

This is implemented by virtue of the approximate positioning determining a start point or an initial position and orientation for subsequent fine positioning and the fine positioning making a position initially determined within the scope of approximate positioning more precise.

Consequently, approximate positioning represents a first positioning and fine positioning represents a subsequent positioning.

Thus, approximate positioning means that the spectacle frame is initially positioned at position that approaches a final position achieved following the fine positioning, for example, approaches this to within a range of 20 mm, 10 mm or less, in relation to the dimensions of the head. Then, fine positioning alters this position to form the final position. Here, the approximate positioning is based on the metadata while the models themselves are used for the fine positioning.

By using the head metadata and the frame metadata for the approximate positioning, the approximate positioning can be implemented quickly and with comparatively little computational outlay. Moreover, the approximate positioning yields a start point or an initial position and orientation for the subsequent fine positioning; this can accelerate the fine positioning since said fine positioning is started from an already approximately correct position of the spectacle frame. This reduces the risk of finding a position that does not correspond to the desired optimum during the fine positioning. By virtue of the 3D models of the head and of the frame itself being used for the fine positioning, this then allows a high accuracy to be achieved during the fine positioning, wherein, on account of the preceding approximate positioning, the fine positioning overall then requires less computational outlay.

Here, a 3D model should be understood to mean a three-dimensional representation of real objects, which are available as a data record in a storage medium, for example a memory of a computer or a data medium. By way of example, such a three-dimensional representation can comprise a 3D mesh, consisting of a set of 3D points, which are also referred to as vertices, and connections between the points, which connections are also referred to as edges. In the simplest case, these connections form a triangle mesh. Such representation as a 3D mesh only describes the surface of an object and not the volume. The mesh need not necessarily be closed. Thus, if the head, for example, is described in the form of a mesh, it appears like a mask. Details in respect of such 3D models are found in Rau J-Y, Yeh P-C, "A Semi-Automatic Image-Based Close Range 3D Modeling Pipeline Using a Multi-Camera Configuration." Sensors (Basel, Switzerland). 2012; 12(8):11271-11293. doi:10.3390/s120811271; in particular page 11289, FIG. "FIG. 16".)

A voxel grid, which represents a volume-type representation, is a further option for representing a 3D model. Here, the space is divided into small cubes or cuboids, which are referred to as voxels. In the simplest case, the presence or absence of the object to be represented is stored in the form of a binary value (1 or 0) for each voxel. In the case of an edge length of the voxels of 1 mm and a volume of 300 mm×300 mm×300 mm, which represents a typical volume for a head, a total of 27 million such voxels is consequently obtained. Such voxel grids are described in, e.g., M. Nieβner, M. Zollhöfer, S. Izadi, and M. Stamminger, "Real-time 3D reconstruction at scale using voxel hashing." ACM Trans. Graph. 32, 6, Article 169 (November 2013), available at the url doi.org/10.1145/2508363.2508374.

Further possible forms of representation of a 3D model include point clouds, for example without information items in respect of the connections between the points (edges, e.g., triangle mesh, see above), a point cloud with a normal vector at each point, representations in the form of spline surfaces and partial surfaces of basic geometric bodies such as spheres, cylinders, planes. The methods described here can be independent of the chosen form of representation of the 3D model.

A spline surface is understood to mean a surface that is described by one or more splines, as described on the internet site with the url en.wikipedia.org/w/index.php?title=B-spline&oldid=840787047.

Basic geometric bodies are understood to mean three-dimensional figures that are described by their surfaces, as described in on the internet sited with the url de.wikipedia.org/w/index.php?title=K % C3% B6rper_(Geometrie)&oldid=177672595.

A point cloud with N points denotes a total of N points, where each of the N points is described by three coordinates.

A normal vector is a vector that is orthogonal (perpendicular) to a straight line, curve, plane or (curved) surface of such an object or combination of such objects.

In particular, the 3D model of the head and/or the 3D model of the spectacle frame can be a 3D model with texture. A 3D model with texture is understood to mean a 3D model which additionally contains the color information items of the surface points of the real object. The use of a 3D model with texture facilitates a true-color representation of the head and the spectacle frame.

Here, the color information item can be contained directly in the vertices as an attribute, for example as an RGB (red green blue) color value, or a pair of texture coordinates is attached to each vertex as an attribute. Then, these coordinates should be understood to be image coordinates (pixel positions) in an additional texture image. Then, the texture of the aforementioned triangles of the triangle mesh, for example, is generated by interpolation from the pixels of the texture image.

When stored as a voxel grid, the color information item can be stored in the voxels themselves. Then, the resolution of the texture corresponds to the size of voxels in the voxel representation. For high-resolution textures, the voxel grid has to be converted into a mesh that describes the surface; this is referred to as a surface reconstruction. (see, e.g., Cignoni, Paolo, et al. "Meshlab: an open-source mesh processing tool." Eurographics Italian Chapter Conference. vol. 2008. 2008.)

Metadata should be understood to mean data that contain information items about the features of the model but not the model itself. In particular, the metadata may supply additional information items for the models and/or contain prominent points or curves on the basis of the respective model. Metadata are also explained in general terms in the German "Metadaten" Wikipedia article, as of Mar. 5, 2017. Provided nothing else is specified, references to Wikipedia refer to the German language Wikipedia (de.wikipedia.org).

As a result of using such metadata, which may have been created in advance, quick positioning of the spectacle frame on the head and also changing of the position thereof is possible in a simple manner, as explained above, in comparison with the use of complete 3D models, which are typically substantially more comprehensive.

The positioning is "virtual" because the process is carried out on a calculation device such as a computer and the real spectacle frame is not placed on the real head.

Preferably, particularly in the fifth aspect of the disclosure but without being restricted to this aspect of the disclosure only, the frame metadata in this case comprise first resting information items, which define one or more locations on the spectacle frame where the spectacle frame rests on the head, and/or the head metadata in this case comprise second resting information items, which define one or more locations on the head where the spectacle frame rests on the head. Here, points, sets of points, curves or areas can be referred to as locations. The virtual fitting of the spectacle frame can be accelerated by means of such first and/or second resting information items since the entire 3D model of the spectacle frame need not be considered for all calculations and steps during the fitting.

Methods described below and above for points, sets of points and curves can be applied accordingly in cases where locations are defined as areas. Component parts, for example the earpiece in the region of the contact area, can be approximated by a hypersphere in relation to a spatial curve. Then, the same method can be used as in the resting curve; however, a fixed distance from the spatial curve can in addition be demanded or forced in the method by mathematical methods.

By preference, particularly in the fourth and fifth aspect of the disclosure but not restricted to these aspects of the disclosure only, the first resting information items comprise a resting point, which denotes a point in the region of a nose bridge of the spectacle frame, in particular in a center of the nose bridge of the spectacle frame, and a resting region, which denotes a region of the earpieces of the spectacle frame.

The terms nose bridge and earpiece are used here as per the terms in DIN EN ISO 8624:2015-12, published in December 2015, and DIN EN ISO 7998:2006-01, published in January 2006.

A resting point is understood to mean a point on the head that defines a contact point of the spectacle frame with the head.

A resting region is understood to mean a region that defines a contact area of the spectacle frame with the head. By way of example, an ear resting region, or resting regions for the ears of the head, can be used for an ear.

A potential resting region, for example a potential ear resting region, is understood to mean a region that, in principle, is suitable as a resting region, for example a region of a spectacle frame that is provided as a resting region for different head shapes.

Resting points and resting region can be stored as metadata.

Approximate positioning of the spectacle frame on the head can be implemented by means of such a resting point. The approximate positioning can likewise be assisted by means of the resting region, particularly even if shape changes of the spectacle frame, described below, as a result of bending and/or position changes of the earpieces are required. Here, the nose bridge and earpieces are parts of the spectacle frame where the spectacle frame typically rests on the head, and so this choice of metadata easily allows positioning that corresponds to the actual conditions to be undertaken.

Here, the frame metadata can be determined in advance together with the 3D model of the spectacle frame for a multiplicity of different spectacle frames and can be stored in a storage medium, and can then be called for carrying out the method. This allows the data to be available quickly.

By way of example, the 3D model of the head can be created by means of stereoscopic image recordings. In such stereoscopic image recordings, an object, in this case the head, is recorded from a plurality of directions, with the recording positions being known. This can be implemented by way of a plurality of cameras that are rigidly disposed with respect to one another. Then, by way of identifying features corresponding to one another in the recorded images, the model can be created by taking account of the known recording positions. More details in respect of such a determination of 3D models is found in, e.g., H. Hirschmüller, "Stereo Processing by Semiglobal Matching and Mutual Information" in IEEE Transactions on Pattern Analysis and Machine Intelligence, vol. 30, no. 2, pp. 328-341, February 2008.doi: 10.1109/TPAMI.2007.1166).

By way of example, the 3D model of the spectacle frame can be provided on part of the manufacturer.

There are various options for determining the frame metadata, wherein the various options may also be combined with one another. By way of example, different metadata of the frame metadata can be determined using different options. These options will now be explained.

The frame metadata are determined by hand in some embodiments. Such manual determination allows the frame metadata to be determined without great computational outlay and provides a user with complete control over the frame metadata. To this end, a user interface can be provided, the spectacle frame being graphically represented on a display on the basis of the model in the case of said user interface. Then, points and/or contours on the spectacle frame can be manually selected, for example by clicking using a mouse and a correspondingly represented mouse pointer, or by direct marking on a touch-sensitive screen. Here, in particular, the aforementioned resting point can be clicked on as a single point and the resting region can be selected as a contour line or contour polynomial. Moreover, axes of rotations on hinges of the spectacle frame can be marked by hand as metadata.

In another exemplary embodiment, the resting region is automatically determined as, e.g., a contour line on a lower side of each earpiece, for example by an image recognition algorithm. No user input is necessary in this case.

Finally, a fully automatic determination of the frame metadata is provided in other exemplary embodiments. This is preferably implemented using machine learning methods, as described in the German Wikipedia article "Maschinelles Lernen," as of Mar. 8, 2017. Here, metadata that were created by hand or partially by hand for a number of spectacle frames as described above can be used as training data for this machine learning.

In an exemplary embodiment, particularly in the case of the second aspect of the disclosure but not restricted to this aspect of the disclosure only, determining the frame metadata comprises determining, in particular automatically determining, prominent points in the 3D model of the frame. Here, prominent points are points that have certain, pre-defined properties, which may be defined in so-called 3D feature descriptors. 3D feature descriptors denote vectors in IV that describe the properties of a prominent point of a 3D model such that this point can be retrieved in a similar 3D model on the basis of this property vector. It is possible to use sets of points in the surroundings of the prominent point. By way of example, it is possible to span a sphere with a predetermined radius, e.g., 10 mm, with the point as a center and the properties of points lying within this sphere, i.e., the points in this subset of the point cloud, can be examined. By way of example, an eigenvalue analysis can be carried out within the meaning of the principal component analysis. Here, extremal eigenvalues k1 and k2 can then be included as elements in the metadata, for example in the form of a property vector. Here, a property vector is understood to mean a representation of values of metadata. In addition or as alternative thereto, it is also possible to determine the principle curvatures of the surface in the surroundings of the point. Principal curvatures are understood to mean information items as described in the internet article "Hauptkrummung [principle curvature]" available at the url de.wikipedia.org/w/index.php?title=Hauptkr%C3%BCmmung&oldid=172452500. The principal curvatures can likewise be included in the property vector. Alternatively, a histogram can be formed of all points and/or normal vectors of the sphere can be determined. To this end, the sphere can be subdivided into regions (volumes) and the frequency of the points (or normal vectors) located in this region can be ascertained for each region. Alternatively, the relative frequency can be determined. Information items about this frequency, for example in the form of a histogram, can likewise be adopted in the property vector.

Such methods using so-called fast point feature histogram (FPFH) descriptors are described for example, at the url pointclouds.org/documentation/tutorials/fpfh_estimation-.php, retrieved on May 25, 2018.

In particular, such property vectors can be determined with the aid of machine learning: By way of example, a human expert can predetermine prominent points in the 3D model, for example by clicking thereon. By way of example, such regions can be points in the region of the hinge of the frame of a 3D model of a spectacle frame, which can be determined uniquely in all spectacle frames; the software extracts the set of points within a sphere around the clicked points—the set of points and the type of point specified by the user, also referred to as a numerical label, are respectively entered as training data into a machine learning method, e.g., a neural network. The completely trained network is subsequently able to determine respective labels for respective points in a given point cloud and consequently able to identify prominent points and/or able to classify points. By way of example, points that are not prominent can be classified as non-relevant.

Such prominent points represent a comparatively small amount of data and established algorithms can be used to determine the prominent points. More details in respect of such a determination of prominent points by means of 3D feature descriptors is described in, e.g., Samuele Salti, Federico Tombari, Riccardo Spezialetti, and Luigi Di Stefano, 2015. Learning a Descriptor-Specific 3D Keypoint Detector. In Proceedings of the 2015 IEEE International Conference on Computer Vision (ICCV) (ICCV '15). IEEE Computer Society, Washington, D.C., USA, 2318-2326, available at the url dx.doi.org/10.1109/ICCV.2015.267. Such predetermined properties may contain, for example, a curvature of the model in the neighborhood of the points. Examples of 3D features descriptors are so-called "fast point feature histograms" (FPFH), as are described in R. B. Ruso "Semantic 3D Object Maps for Everyday Manipulation in Human Living Environments," Dissertation, TU Munich 2009, pages 57ff.

Prominent curves may also be defined accordingly. Prominent curves can be defined as 3D curves. A 3D curve is a representation of a curve in three-dimensional space. 3D curves can be stored by a list of 3D points; alternatively, the 3D curves may also be represented by a polynomial curve, in some exemplary embodiments with an orthogonal basis, e.g., as a Legendre polynomial basis. In other exemplary embodiments, the curves can be represented as spline curves, represented with the aid of the B-spline basis functions, as described in the internet articles available at the url de.wikipedia.org/w/index.php?title=Legendre-Polynom&oldid=172427311 and at the url en.wikipedia.org/w/index.php?title=B-spline&oldid=840787047.

By way of example, the resting region of the earpieces can be described with the aid of such prominent curves; here, a point in the curve can be brought into correspondence with the resting point at the ear. In such exemplary embodiments, the curve is part of the metadata of the frame and, for example, runs along the lower side of the earpiece and describes the entire possible resting region.

Prominent points determined thus are then classified as relevant and non-relevant points according to the second aspect of the disclosure. Relevant points are understood to mean points that are used to represent metadata. In particular, relevant points can represent the required metadata without redundancy or with as little redundancy as possible.

Non-relevant points are understood to be points that either represent no metadata or have less relevance, for example because the meta information items represented by the non-relevant point are likewise represented by other points, i.e., a redundancy of information items is present.

In manual methods, the user can determine the relevant points whereas the number of relevant points can be predetermined as a target in automated methods; non-learning-based machine methods can also determine, for each prominent point, a measure for the "saliency" of this point. By way of example, if principle curvatures are used as a property of surfaces, the product of the two principal curvatures can be used as a measure. Learning-based machine methods can imitate the manual selection, wherein the relevant points can be predetermined by the training phase.

Thus, the following steps can be restricted to the relevant points, and so the amount of data to be processed is reduced. This can be implemented, in particular, using supervised learning methods, as described in the German Wikipedia article "Uberwachtes Lernen," as of Mar. 8, 2017. Here, the points identified during the determination of prominent points are displayed on a display, for example with a representation of the frame, and the respective points can then be manually assigned point classes. These point classes can then be linked to the 3D feature descriptor for the respective point.

Then, this link can be stored as a data record for each frame, for example as an XML file.

The point classes specify the element of the spectacle frame specified by the respective point or where the respective point is located on the spectacle frame. Examples of point classes include, for example, "outer side of the left hinge, top" for a point located on the outside and at the top of the left spectacle hinge, "outer side of the left hinge, bottom" for a corresponding point located at the bottom, corresponding classes for the right hinge, "bridge center, front" for a center of the nose bridge on the front side, "bridge center, back" for a point on the nose bridge on a back side, etc. Here, the front side is the side of the spectacle frame distant from the head of the person donning the spectacle frame when said spectacle frame is donned, and the back side is the side of the spectacle frame facing the head of the person.

In the case of assisted learning, there are various possible algorithms for converting the point classes, learned in this way for the prominent points, into a model and for applying this model in order to then, following the learning phase, automatically ascertain the respective point class for a point found using a 3D feature descriptor. In this respect, see also "Machine Learning Overview" by Open Source Computer Vision, Docs.opencv.org//3.1.0/dc/ddb/ml_intro.html, as of Mar. 8, 2017. Examples of algorithms include a random forest algorithm (see Breiman, Leo, "Random forests." Machine learning 45.1 (2001): 5-32.), e.g., as implemented by the class "cv::ml::RTrees" in the software library "Open CV", which can be used for training and for classifying; see the url "docs.opencv.org/3.1.0/d0/d65/classcv_1_1ml_1_1RTrees.html". This is an example of the random forest method. Another random forest method can be introduced in MATLAB by means of the TreeBagger class.

A further possible algorithm lies in the use of a so-called "support vector machine (SVM)", as is likewise provided in the aforementioned Open CV software library.

Prominent points then can be identified automatically by means of such algorithms; this simplifies the processing of the 3D model of the spectacle frame since, following the training phase, user inputs are no longer necessary for the identification of the prominent points.

Preferably, a coordinate transformation is carried out following the identification and classification of the prominent points. Such a coordinate transformation allows frame metadata and/or 3D models of the frame for different frames to be transferred into a common coordinate system. This simplifies the subsequent processing since the same coordinate system can be assumed for every spectacle frame.

In some exemplary embodiments, such a coordinate transformation is carried out by means of a principal component analysis on the set of prominent points classified as relevant. The principal component analysis (PCA) is described, for example, in the Wikipedia articles available at the url de.wikipedia.org/wiki/Hauptkomponentenanalyse and the url en.wikipedia.org/wiki/Principal component analysis. In the case of a set of points X of n points in space, it is possible, for example, to form a matrix X with n rows and 3 columns (for x, y and z coordinates of the respective n points). Then, it is possible to examine the 3×3 matrix $X'^*X$ and the principal components can be determined as the largest eigenvectors of this matrix.

A principal axis transformation is understood to mean a coordinate transformation into the coordinate system spanned by the principal components.

Another option for the coordinate transformation lies in a rule-based coordinate transformation by a fixed assignment of a coordinate origin and directions of coordinate axes on the basis of the prominent points. A rule-based coordinate transformation is understood to mean a linear combination of prominent points for defining the basis vectors of the target coordinate system, i.e., of the coordinate system into which the transformation takes place. By way of example, a prominent point of the aforementioned "bridge center, front" class can serve as a coordinate origin and difference vectors between predetermined points or linear combination of such difference vectors can serve as coordinate axes. Thus, the difference between a point of the aforementioned "outer side of the right hinge, top" class and a point in the "outer side of the left hinge, top" class can be used as a coordinate axis. Here, it may be advantageous if the prominent points are uniquely determined and/or available in a fixed sequence. By way of example, this may be the case in the case of manually set points, which are set, for example, by selection by a user.

In such a coordinate system with a center of the nose bridge as the origin, a plane of symmetry of the spectacle frame then runs through this origin. For explanations in the following, the assumption is made that the spectacle earpieces of the spectacle frame are oriented substantially in the z-direction, a connecting line between the hinges of the spectacle frame is parallel to the x-axis and a y-direction is perpendicular thereto. Expressed differently, a horizontal direction corresponding to a connecting line between the eyes of the head, in particular between pupil centers of eyes of the head, in a main fixation direction is defined as x-direction when the head is held erect, a vertical direction is defined as y-direction and a direction perpendicular to the x- and y-direction is defined as z-direction.

In exemplary embodiments where the position of pupil centers of the eyes of the head in a main fixation direction is not known, the connecting line of the eyes of the head can also be defined differently, for example on the basis of the eye positions of the 3D model.

The head being held erect is understood to mean that the head is held in such a way that the connecting line of the eyes lies in a plane parallel to the frontal plane of the head and the vertical direction lies parallel to the line of intersection between frontal plane and sagittal plane. The 3D model of the head can be disposed in such a way that the 3D model of the head is in an erect position.

Frontal plane and sagittal plane are defined on the Wikipedia internet sites at the url de.wikipedia.org/w/index.php?title=Frontalebene&oldid=177246560 and the url de.wikipedia.org/w/index.php?title=Transversalebene&oldid=177246519.

In some examples, the coordinate system may be fixedly connected to the head such that, for example when the head is tilted, the relationship in terms of position and orientation between the coordinate system and the head remains unchanged, i.e., for example, that the x-direction still extends in accordance with the connecting line between the eyes of the head. Expressed differently, the head can be disposed in the coordinate system in stationary fashion.

Here, the reference to the head being held erect serves to define the coordinate system of x-direction, y-direction and z-direction. Here, the z-axis, as a rule, extends parallel to the main fixation direction.

Then, the aforementioned plane of symmetry is the yz-plane. However, this coordinate system only serves as an example and other arrangements of the axes are also possible, as is the use of spherical coordinates instead of Cartesian coordinates.

Then, predetermined components of the spectacle frame are localized in one exemplary embodiment. In particular, the position of nose bridges and hinges of the spectacle frame can be determined. This can be implemented on the basis of the classified prominent points, which, as already explained above, may be selected manually or else may be determined automatically, as described above. By way of example, the position of the hinges of the pair of spectacles can be determined on the basis of prominent points that were determined on the outside or inside of the hinges, in particular by points of classes such as "outer side of the left hinge, top" and "outer side of the left hinge, bottom" as described above. In one exemplary embodiment, a hinge axis point is calculated as a mean value of such prominent points. In particular, a left hinge axis point can be calculated according to Left hinge axis point=¼*(outer side of left hinge, top+outer side of the left hinge, bottom+inner side of left hinge, top+inner side of the left hinge, bottom), where the left hinge axis point denotes the position of a hinge axis point on a left side of the spectacle frame, and outer side of left hinge, top, outer side of left hinge, bottom, inner side of left hinge, top, and inner side of left hinge, bottom denote prominent points of corresponding point classes; i.e., points that are located top left on the outside of the left spectacle hinge, bottom left, and that are each situated on the inside and on the outside (on an inner side of the spectacle frame, i.e., toward the nose bridge, and on an outer side of the spectacle frame, i.e., away from the nose bridge). A corresponding formula can be used for the right hinge axis point by virtue of the points on the left side being replaced by points on the right side. In this way, it is possible to determine a hinge axis point, which lies on the hinge axis in the interior of the spectacle frame, on the basis of points visible from the outside.

The nose bridge can be defined in a similar way as intersection of the points of the "bridge center, front" and "bridge center, back" classes, as explained above.

In some exemplary embodiments, in particular according to the fourth aspect of the disclosure but not restricted to this aspect of the disclosure only, the 3D model of the frame is segmented into components for the purposes of determining the frame metadata, wherein the components may comprise, in particular, components for the spectacle earpieces and components that describe the spectacle frame apart from the spectacle earpieces. Segmenting a 3D model is understood to mean a division of the information items into subsets, for example subdividing 3D point clouds into subsets of 3D point clouds.

Such a segmentation allows the various components to be analyzed individually for the purposes of determining frame metadata, thereby reducing the amount of data to be processed. In particular, the segmentation can be carried out here on the basis of the prominent points and/or on the basis of the localization of the nose bridge and/or hinges, as explained above.

To this end, sectional planes can be defined in space, said sectional planes dividing the points (vertices) or voxels of the 3D model.

Here, the sectional planes can be defined by a respective reference point p and a normal vector n, which is perpendicular to the plane. Here, reference point p represents a support for a plane that, together with a normal vector n, uniquely denotes the position and orientation of the plane with respect to the origin of the coordinate system. The reference point can be available as a vector. Likewise, coordinates can be represented as vectors from the coordinate system origin to the coordinates of the point. Then, for a vertex or voxel of the 3D model, the position of which are defined by coordinates v (corresponding to the Cartesian coordinate representation of the point), the following applies: $\langle v, n\rangle \leq \langle p, n\rangle$ or $\langle v, n\rangle > \langle p, n\rangle$. Here, $\langle , \rangle$ denotes the Euclidean scalar product. Scalar product means the Euclidean scalar product, but also use can be made of differently defined scalar products. Here, the normal vector n is normalized to a length of 1, i.e., $\langle n, n\rangle = 1$.

Depending on which of the two relations applies, the point v is located on one side or the other side of the sectional plane. This facilitates a simple segmentation into components according to the third aspect of the disclosure, without being restricted thereto.

For the purposes of segmenting the spectacle frame, the respective hinge axis point, which may be determined as described above, can be used as reference point of the sectional plane in this procedure. The z-axis of the coordinate system, i.e., the direction in which the spectacle earpieces extend, can then serve as normal vector for the sectional plane in the aforementioned coordinate transformation. The vertices or voxels for which $\langle v, n\rangle \leq \langle p, n\rangle$ holds true then define the respective spectacle earpiece.

Then, further metadata can be calculated on the basis of the components segmented from the 3D model of the spectacle frame in this way. Thus, the aforementioned resting region of the resting information items can be calculated on the basis of the spectacle earpieces segmented from the 3D model of the spectacle frame. Using the segmented components means that less data has to be used when determining the metadata than in the case where the complete 3D model is used, as a result of which the calculation can be accelerated.

For the purposes of determining the resting region, the following method can be used according to the fourth aspect of the disclosure for each of the spectacle earpieces segmented from the 3D model of the spectacle frame:

Initially, a start point a and an endpoint b of the respective spectacle earpiece are determined from the respective segmented spectacle earpiece of the 3D model of the spectacle frame. Start point and end point of the spectacle earpiece frame in this case mean the start and end point of the region that is provided as an ear resting region. In the aforementioned coordinate system, the point of the segmented spectacle earpiece which has a minimum value in its z-component can be the start point a and a point which has a maximum value of the z-component can be the endpoint b. The determination can be implemented manually, for example by a user selection from the 3D model, or in a rule-based manner, for example by virtue of a fixed distance from the resting point being required in both direction, or as a required relative distance in relation to the ends of the earpieces.

A potential ear resting region is determined next. Z-components of planes that restrict this potential ear resting region can be used as a predetermined ratio $\alpha$ and $\beta$ relative to the length of the spectacle earpiece in the z-direction, and so the following applies:

$$\alpha < (v_z - a_z)/l_z < \beta.$$

Here, $\alpha$ and $\beta$ are predetermined values, which may, for example, be predetermined on part of the manufacturer for a respective spectacle frame or else be determined as empirical values from many spectacle frames. $\alpha$ can lie between 0.3 and 0.6, e.g., $\alpha=0.47$, and $\beta$ can lie between 0.6 and 0.9, e.g., $\beta=0.76$.

$a_z$ is the z-component of the point a, and $l_z$ is the length of the spectacle earpiece in the z-direction, corresponding to $b_z - a_z$. $v_z$ is the z-component of a vertex or voxel of the 3D model. Vertices or voxels, for the z-components $v_z$ of which the aforementioned relationship applies, belong to the potential ear resting region; i.e., the following applies to these vertices or voxels:

$v_z > \alpha \times l_z + a_z$ and $v_z < \beta \times l_z + a_z$.

The resting region can then be ascertained as a resting point set or resting curve by means of a calculation with an incrementally sliding window. A resting point set means the set of points that form the resting region or a subset thereof.

A resting curve is a representation of the resting points as a 3D curve. Window means a certain three-dimensional region in which points are considered. To this end, a window with a fixed width (e.g., a width of between 0.5 mm and 3 mm, e.g., 1 mm in the z-direction) and a fixed increment (e.g., likewise between 0.5 mm and 3 mm, for example approximately 1 mm) is slid over the potential ear resting region in the z-direction. Initially, the set of vertices or voxels of the potential resting region that are located in the window is ascertained for each position of the window. Subsequently, the scalar product s with a direction vector d is formed for each of these vertices or voxels, s=<v, d>, where v again specifies the coordinates of the vertex or the voxel.

As a rule, a maximum ŝ of these scalar products s is uniquely assigned to an assigned vertex or voxels with coordinates v̂. Should a plurality of maximum scalar products be present in one window, a predetermined vertex or voxel, for example the vertex or voxel with the maximum value calculated first, is taken as a vertex or voxel v for this window. The set of coordinates v̂ found thus for all windows, for example ordered according to increasing z-value, yields an arrangement of points that characterize the resting region according to the fifth aspect of the disclosure, without being restricted thereto, as a resting curve. In exemplary embodiments, this curve can be smoothed by filters, for example by means of a Gaussian filter, or a curve can be fitted to the points; by way of example, a spline approximation can be carried out by means of B-splines, as described in the German Wikipedia article "Spline" as of Mar. 9, 2017.

A normalized vector is assumed as direction vector d, i.e., <d, d>=1. The latter can be chosen to be fixed, respectively for the left and right spectacle earpiece. An example for a fixed direction vector would be the vector (0, −1, 0) in the above-defined coordinate system. In this case, the resting point would always be the lowest point of the spectacle earpiece. The position and orientation of the earpiece becomes more precise in the case of an inwardly directed resting curve, i.e., $d=(\cos(\sigma), \sin(\sigma), 0)$ for $\sigma=30°$ for the right earpiece, and $d=(-\cos(\sigma), \sin(\sigma), 0)$ for $\sigma=30°$ for the left earpiece.

In some exemplary embodiments, the head metadata contain an ear resting point, which is chosen by a manual selection of a point on a representation of the ears of the model, for example. For the purposes of determining the direction vector d, a window can be chosen in this case around this ear resting point in the 3D model of the head, for example all of the vertices or voxels that have a z-value that is spaced apart from this ear resting point by no more than a predetermined distance, for example no more than between 0.25 mm and 1 mm, for example no more than 0.5 mm. Then, the mean value of all these vertices of the window is determined and the normalized difference vector of the ear resting point minus mean value is defined as direction vector d.

In this way, a resting curve as a resting region can be determined automatically in a relatively simple manner and this can then be used in further steps of the method for positioning the spectacle frame on the head, as will still be explained in more detail below.

In order to accelerate the fit, the frame metadata may moreover comprise expected ear resting points on the spectacle earpieces, which may be selected manually. These expected ear resting points can then serve as a start point for the virtual positioning of the pair of spectacles; i.e., the pair of spectacles are initially placed on the ears at these points. This may accelerate the virtual positioning.

Moreover, the metadata in the case of spectacle frames comprising nose pads may comprise points that denote the positions of such nose pads. These points, too, may be selected manually or determined by machine learning.

By way of example, a point clicked on by the user can be assumed to be the center of the nose pad. A sphere with a predetermined radius, for example with a radius of 6 mm, can be drawn around said point. Then, points situated within this sphere can be analyzed by means of principal component analysis, as already described above.

In order to analyze such point clouds, it is possible, in particular, to subtract the sphere center from the coordinates of the point cloud prior to analysis in order to obtain a set of points centered around an origin. This may simplify the subsequent analysis.

The frame metadata may moreover comprise bending information items in respect of a flexibility of the frame, in particular of the spectacle earpieces. Using such information items, the spectacle can then be fitted virtually to the head by bending during the virtual positioning and these adaptations can then be applied to a corresponding real spectacle frame. Examples of such information items include, for example, an information item as to whether, and, if so, how far, a rotation about hinge axes is possible (e.g., in the case of plastic frames with a spring-mounted hinge). Spectacle hinges have a stop—e.g., at the maximum opening of 180 degrees. In some hinges, this stop can be realized by means of a spring, and so an opening beyond 180 degrees is possible. In the case of a solid stop without a spring, the earpiece is deformed when bent open. Thus, e.g., a type of hinge—i.e., fixed or sprung—is encoded in the information item. Additionally, the flexibility of the earpiece is encoded; here, a rigid model of the earpiece is used in the case of sprung hinges. A further example relates to an information item about a possible adjustment of the inclination on the spectacle earpiece; i.e., a rotation of the spectacle earpiece about the x-axis relative to the remainder of the spectacle frame. In many metal frames, this is possible by bending the earpieces upward or downward at the hinges.

This information item may also specify that no adjustment of the inclination is possible. By way of example, this information item may be available as a yes/no information item (adjustment of inclination is possible or not) or else as an angle range within which the inclination can be altered.

Moreover, bending open of the spectacle earpieces themselves can be defined, for example by means of a bending function. By way of example, a multivariate polynomial over the z-axis and an offset in the x- and xy-direction can describe such a bending function. Moreover, it is also possible to model a deformation of the edge of the frame of the spectacle frame caused by bending open the earpieces, for example by way of a multivariate polynomial or a multivariate spline function (e.g., a tensor product of a B-spline basis; see De Boor, Carl, et al. "A practical guide to splines". vol. 27. New York: Springer-Verlag, 1978, Chapter XVII.).

Such bending is possible, in particular, in the case of thin spectacle earpieces or very elastic spectacle earpieces.

The aforementioned information items can be provided for bending and fitting the spectacle earpieces in different directions, for example in the x- and y-direction according to the aforementioned coordinate system.

Variants of, and methods for determining options for, the head metadata according to various exemplary embodiments are discussed next.

Preferably, particularly in the first aspect of the disclosure but not restricted to this aspect of the disclosure only, the head metadata comprise a position of the eyes, which can then be used for horizontal alignment of the spectacle frame. By way of example, these metadata specify the position of the eyes, for example of the pupils, in particular of the pupil centers, in the main fixation direction (see DIN EN ISO 13666:2013-10, 5.33) as point coordinates. Moreover, the head metadata may comprise ear placement points, as already mentioned above, which specify a resting point of the spectacle frames on the ears. Other placement points, which specify a resting point of the spectacle frame on the head, for example a placement point on the nose of the head, are also possible. Simple positioning of the spectacle earpieces on the ears is possible as a result of these metadata.

Moreover, the head metadata may comprise a placement point and/or a description of the nasal bridge, for example in the form of a 3D curve, which describes a region of the nasal bridge, also referred to as nasal bridge region. These metadata may serve for the approximate positioning of the spectacle frame on the head. Here, the placement point is a point at or near the nose in the 3D model of the head, which point can be brought into correspondence with the aforementioned resting point of the frame metadata, in particular by way of approximate positioning.

As already discussed for the frame metadata above, such head metadata may be determined manually, for example by selecting corresponding points or curves in a representation of the head on the basis of the 3D model. However, they may also, in full or in part, be determined automatically, for example by way of machine learning as discussed above.

In other exemplary embodiments, two-dimensional image data of the head are used in addition to the 3D model of the head for the purposes of automatically determining head metadata. Such 2D images are available in any case if the 3D model is created by means of camera recordings of the head from a plurality of calibrated positions. Calibrated positions means that the positions of the image recordings are known, and so the 3D model can then be determined on the basis of the recorded images and the positions. Alternatively, 2D images may also be generated from the 3D model with texture by image synthesis (also referred to as rendering). By way of example, information in this respect can be found in the "Bildsynthese" article in the German Wikipedia, as of Mar. 10, 2017.

Then, facial features of the person such as eyelids, eyebrows, a nasal bridge, eyes and the like can be identified in such 2D images by image recognition methods (also referred to as object detectors). By way of example, suitable methods to this end are provided in the software library "dlib", available at the url "blog.dlib.net/2014/08/real-time-face-pose-estimation.html", as of Mar. 10, 2017, or described in V. Kazemi et al., "One Millisecond Face Alignment with an Ensemble of Regression Trees," X. Zhu et al., "Face detection, pose estimation and landmark localization in the wild," CVPR 2012, also presented on the homepage of the first author and available at the url www.ics.uci.edu/~xzhu/face/ as of Mar. 10, 2017.

These points or regions in the two-dimensional image identified thus are subsequently projected on the 3D model (e.g., the 3D mesh) of the head and are thus available as head metadata in the form of 3D points. In an exemplary embodiment, an inverse projection matrix is used for projection purposes. Here, the projection matrix is composed of a rigid body transformation from the coordinate system of the model, e.g., of the 3D mesh, in the camera coordinate system of the employed camera and the camera matrix. If a camera device with calibrated positions for the image recording is used for recording the 3D model and the 2D image, as described above, these matrices are given or determined within the scope of determining the 3D model from the recorded images (see Richard Hartley and Andrew Zisserman, 2000. Multiple View Geometry in Computer Vision. Cambridge University Press, New York, N.Y., USA.)

In this way, the projection can be implemented quickly since the required matrices are already known from the determination of the 3D model. In an alternative exemplary embodiment, facial features in the 2D images can also be marked by hand, for the purposes of which the 2D image can be presented on a display. Mixed forms are also possible, in which the facial features are determined automatically as explained above and may subsequently be corrected by hand.

The aforementioned nasal bridge region can be provided as a 3D curve. To this end, use can be made of a method corresponding to the method for determining the resting region of the spectacle earpiece, as already described above. In particular, use can be made of the above-described method with a sliding window, wherein a direction of the head (which, for example, may be a coordinate axis such as the z-axis of the 3D model), which is oriented to the back in the head direction, can be used as direction vector d of the aforementioned formulas. This direction can also be determined when determining the head. The direction vector d in this case corresponds to the direction of the head rotation or the viewing direction as described in the European patent application EP 3355102; said direction can be determined by means of a centration appliance that is disclosed in the European patent application EP 3355100; here, the displacement direction of the window is the y-axis of the 3D model of the head—i.e., the vertical axis; the entire model of the head is used or else a section by means of the y-coordinate of the mean value of the pupil position and y-coordinate of the tip of the nose—, determined as v_max, for which the scalar product s=<v, d> (as above) becomes maximal.

As in the case of the resting region, it is also possible here to carry out filtering, for example by means of Gaussian filters, and/or a spline approximation.

Here, the interval on the y-axis is used as a parameterization of the curve of the nasal bridge. Thus, a function is obtained, said function supplying the associated 3D point on the nasal bridge for each y-value.

The aforementioned placement point can then be determined on the basis of this 3D curve for the nasal bridge region, in particular in accordance with the fifth aspect of the disclosure without being restricted to said aspect of the disclosure. To this end, a plane, in which a connecting line of the eye positions of the 3D model lies and in which the viewing direction lies, is intersected by the 3D curve, also referred to as nasal bridge curve, which serves as a start point s for determining the resting point, in one exemplary embodiment. Then, in the surroundings of this point s, for example within a predetermined region (a predetermined distance, for example ±3 mm, ±2 mm etc.), the point of the nasal bridge curve that has the smallest value in the viewing direction, i.e., the point that is situated furthest back (in the direction of the occiput of the 3D model), is determined. A fixed offset in the y-direction can still be added to the y-value of this point in order to ascertain the y-value and the placement point by means of the aforementioned parameterization of the curve. This allows a placement point to be ascertained, the latter being able to be used together with the resting point of the frame metadata for an initial positioning of the spectacle frame, said initial positioning being relatively close to a final position, possibly accelerating a subsequent optimization.

Then, the head metadata can be stored together with the 3D model of the head and can consequently be used for different frames. This saves recalculating the head metadata for various frames.

The virtual positioning on the basis of the metadata can preferably comprise an approximate positioning on the basis of the metadata in order to provide a start point for the subsequent further fitting. Here, in particular, the aforementioned placement point on the nasal bridge can be brought into correspondence with the resting point of the spectacle frame. Here, the z-axis of the frame (i.e., the direction of the spectacle earpieces) can be made congruent with a corresponding axis of the 3D model of the head, which denotes the viewing position.

Following this part of the approximate positioning, the frame can be rotated about the x-axis, i.e., the "as-worn" pantoscopic angle of the frame can be altered, in such a way in one exemplary embodiment that the resting region of the spectacle earpieces rests on the ear resting points. Initially, this is carried out separately for each earpiece. To this end, an intersection of the resting region with a cylinder surface is calculated in one exemplary embodiment, wherein the cylinder axis corresponds with the axis of rotation of the frame (the x-axis in the aforementioned coordinate system). Here, the axis of rotation extends through the resting point. The radius of the cylinder is the distance of the respective ear resting point from the axis of rotation. The point of intersection on the cylinder directly yields the angle through which the frame is inclined forward or inclined back. Here, the cylinder intersection can be calculated by iterative line cylinder intersections. Here, the resting region (e.g., the resting curve ascertained above) may initially be used in a coarser segment representation, i.e., with a lower resolution, in order to accelerate the calculation. By way of example, the connecting line between the aforementioned start point a and end point b can be used as coarser segment representation in the simplest case.

This determination by means of iterative line cylinder intersections can be undertaken as follows: Let S denote the point of intersection of this connecting line with the cylinder. Then, the z-coordinate $z_S$ of S is used during an iterative refinement in order to ascertain an associated real curve point. Although the latter no longer lies on the cylinder surface, it can nevertheless be used as an approximation for determining the angle. Additionally, it is now possible to carry out a further iteration step. To this end, points $k(z_S-\varepsilon)$ and $k(z_S+\varepsilon)$ on the curve with a spacing $\varepsilon$ around $z_S$ are used; these act as new start and end points instead of a and b in the next iteration.

Following this positioning, the frame is bent, for the purposes of which the aforementioned bending information items of the frame metadata, which describe a flexibility of the frame, are used.

To this end, the aforementioned method with cylinder intersections, described above, can be applied again. Should, as discussed above, the bending information item be available as a multivariate bending function, it is possible to carry out an optimization in which a distance of the ear resting point from the resting region of the earpiece is used as a cost function. Here, in general, a cost function is a function that changes as a function of one or more parameters to be optimized and that is brought to a maximum or minimum for optimization purposes. Here, the parameter of the bending function responsible for the strength of bending is chosen as parameter to be optimized. In the case of a simple polynomial bending function for the bending-open in the x direction, the mathematical inverse function can likewise be approximated by a polynomial. To this end, the bending function $D_z(x)$ is modeled in additive fashion as a polynomial at the position z for bending in the x-direction; the inverse function $D_z^{-1}(d)$ thereof is likewise approximated by polynomial, for example by sampling the function at individual discrete points [x1, x2, . . . , xn] and carrying out a new polynomial approximation on $[D_z(x1), D_z(x2), \ldots, D_z(xn)]$ with values $[D_z^{-1}(Di(x1)), D_z^{-1}(D_z(z2)), \ldots, D_z^{-1}(D_z(xn))]$. In this case, the bending-open of the resting curve to the x-value of the ear placement point can be ascertained directly by virtue of applying the inverse function for z=resting position and x=difference between ear placement and resting point.

Bending the frame also allows the inclination to be fitted to the earpiece by way of rotation in the z-direction (i.e., bending the earpiece about the x-axis). Here, too, use can be made yet again of the aforementioned cylinder intersection method, wherein the ear placement point is used for constructing the cylinder and the latter is intersected by the resting curve.

In an exemplary embodiment according to the first aspect of the disclosure, without being restricted to this aspect of the disclosure only, the fine positioning of the frame is at least substantially restricted to an xy-plane. Here, an xy-plane is understood to mean a plane extending parallel to the x-direction and to the y-direction, said plane thus being spanned by two vectors, one vector of which extending in the x-direction and one vector extending in the y-direction, and said plane consequently being perpendicular to the z-direction. Then, a vector in the z-direction is a normal vector of the xy-plane. A displacement in the xy-plane can also be denoted as a displacement in the x-y-direction. In particular, the xy-plane may comprise the anchor point of the spectacle frame following the approximate positioning.

Here, restricting the fine positioning at least substantially to the xy-plane means that a change in position in the z-direction is at least no more than 10% or no more than 5% of the change in position in the xy-plane; in particular, said change in position in the z-direction may also be 0. Here, the frame is displaced in the x-y-direction until no collision is present between the 3D model of the spectacle frame and the 3D model of the head.

A change in position of the spectacle frame can be brought about by displacing the spectacle frame.

Displacing the spectacle frame is understood to mean a translational movement of the spectacle frame, which may be characterized by displacement vector. The displacement vector may describe the displacement between the initial position and orientation of the spectacle frame obtained by the approximate positioning and the position of the spectacle frame at the end of the fine positioning step.

The length of the displacement vector can be referred to as the distance of the displacement. Here, in some exemplary embodiments, the spectacle frame can be displaced by a first distance in the xy-plane and can then be displaced by a second distance along the z-direction. As described above, the displacement can be restricted at least substantially to the xy-plane. By way of example, this may mean that, in some exemplary embodiments, the second distance is no more than 10% of the first distance. In some exemplary embodiments, the second distance is no more than 5% of the first distance. In some exemplary embodiments, the second distance is 0% of the first distance.

The surface of the 3D model of the head can be slightly lowered for this fine positioning (for example, between 0.3 mm and 1 mm) in order to take account of a deformation of the skin at the resting areas of the spectacle frame. This can facilitate more realistic fitting. In this case, no collision means of the 3D model of the frame and the 3D model of the head have no common spatial regions. Following the fine positioning, the aforementioned bending process can be carried out again in order to further improve the fitting.

In an exemplary embodiment, a suitability in principle of the spectacle frame for the respective head can be ascertained after this step by virtue of checking whether a lower edge of the spectacle frame collides with a cheek region of the head in the respective models.

In the case of frames with nose pads, as are often present in metal frames, the virtual positioning may further comprise the positioning of the nose pads. In one exemplary embodiment, this fitting is modeled as a rotation of the nose pads about a center of rotation. To this end, the nose pads can be segmented from the remaining part of the spectacle frame; this may be carried out as mentioned above. This fitting can be presented following the aforementioned bending. Fine positioning can be carried out anew following any change in the nose pads.

Principal axes of the nose pads can be chosen as axes of rotation; by way of example, these may be determined using the aforementioned principal component analysis. The rotation can be restricted to two angles about the two principal axes, emerging from the principal component analysis, for the largest eigenvalues. An inverse of the area where the nose pads contact the nose can be used as a cost function for optimizing the position of the nose pads in order to achieve a rest that is as wide as possible. This allows virtual fitting of the position of the nose pads as well, which may then be transferred to a real frame. As result of this, fitting the nose pads on the real frame to the real head is no longer necessary or only still necessary to a very small extent.

In some exemplary embodiments, a certain pre-adjustable "as worn" pantoscopic angle (e.g., 9°) can be predetermined during this change in the inclination. This fixed "as-worn" pantoscopic angle then is maintained by changing the inclination, even if the pair of spectacles is subsequently displaced, as will be explained in more detail below.

Displaying the head with the spectacle frame positioned thereon can be implemented by means of conventional image synthesis methods; see the aforementioned German Wikipedia article relating to image synthesis. To this end, camera images, in particular, can be used as a texture, said camera images also having served to create the 3D model, as this yields a natural image impression. An illumination can be set or predetermined for the image synthesis and the image synthesis can then be implemented by means of so-called ray tracing, for example; see the Wikipedia article on "Ray Tracing" as of Mar. 10, 2017.

To this end, use can be made of virtual light sources that correspond to an ambient illumination when the images of the head were recorded. Preferably, this ambient illumination is determined when the images are recorded. In order to determine this ambient illumination, a panoramic camera (i.e., panoramic camera with a large viewing angle), in particular, can be used in the camera system used for recording images for creating the 3D model of the head, said panoramic camera recording the surroundings for the purposes of identifying light sources. In other exemplary embodiments, such systems for recording images for creating the 3D model may have an illumination device in a known position, which is then also used as a position of an illumination for the image synthesis. Spectacle lenses in the frame may also be considered during this image synthesis in order to provide the observer with an image impression that is as natural as possible. In this case, reflections that arise when mirroring layers are used, in particular, can be taken into account. In an exemplary embodiment, models are available for different types of antireflection coatings, and also models for different types of glass in order to provide the user an impression about different layers. Within the scope of image synthesis, the effect of antireflection layers appears, in particular, in the form of reflections in a side view.

Furthermore, the method may comprise a change in the position of the spectacle frame on the basis of user inputs. Thus, the user can adapt the seat of a pair of spectacles according to their wishes or an optician can still undertake modifications. To this end, a suitable user interface can be provided for the user; by way of example, navigation can be implemented by mouse movements or by touching a touch-sensitive screen (touchpad).

The method can be combined with other methods for fitting a pair of spectacles, for example centering methods, as are described in the European patent application number EP 3355103, for example. Here, in particular, virtual centering according to the methods described therein can be undertaken after the fitting of the frame as discussed above; this improves the accuracy of the centering.

If, during this interaction, the user selects a placement point of the spectacle frame on the nose that deviates from the placement point in the metadata, the placement point in the metadata can be altered to the placement point chosen by the user. This altered placement point, which is preferred by the user, can then be used during the virtual fitting of further frames.

During the interaction, the user can rotate the model and observe it from the side. In the process, the rotation can be restricted such that, for example, regions that have no texture available, such as an occiput of the user, are not observable. To this end, for example, a virtual observation position can approach the 3D model of the head in the case of a movement in the direction of the occiput and/or the sensitivity of the user in relation to the input of the user (mouse pointer, touchpad and the like) can deteriorate during the rotation in the direction of the occiput. Moreover, the user may also rotate the frame about the x-y-axis in order to take account of asymmetries in the face.

The aforementioned method can be carried out by means of an apparatus for virtual fitting of a pair of spectacles, said apparatus comprising a processor and a display, wherein a corresponding computer program with program code for carrying out the method runs on the processor. The computer program may be stored on a memory of the apparatus or may else be provided via a cloud. Here, it should be noted that the computing device may also be implemented by means of a distributed system, which has various separate components. By way of example, calculating the metadata or calculating the model of the head from recorded image data can be carried out on a comparatively powerful computer, for example an external server which may also include co-processors such as graphics processors. By using the metadata, the positioning of the pair of spectacles on the head and the subsequent representation is less computationally intensive, and so this is also performable on less powerful units, such as, e.g., mobile terminals such as tablets or smartphones, in corresponding application programs or else by means of a browser via the Internet.

BRIEF DESCRIPTION OF THE DRAWINGS

The disclosure will now be described with reference to the drawings wherein:

FIGS. 3A to 3C show views for elucidating 3D models of a head;

FIG. 4 shows an illustration for elucidating a 3D model of a spectacle frame;

DESCRIPTION OF EXEMPLARY EMBODIMENTS

Figure 1A:
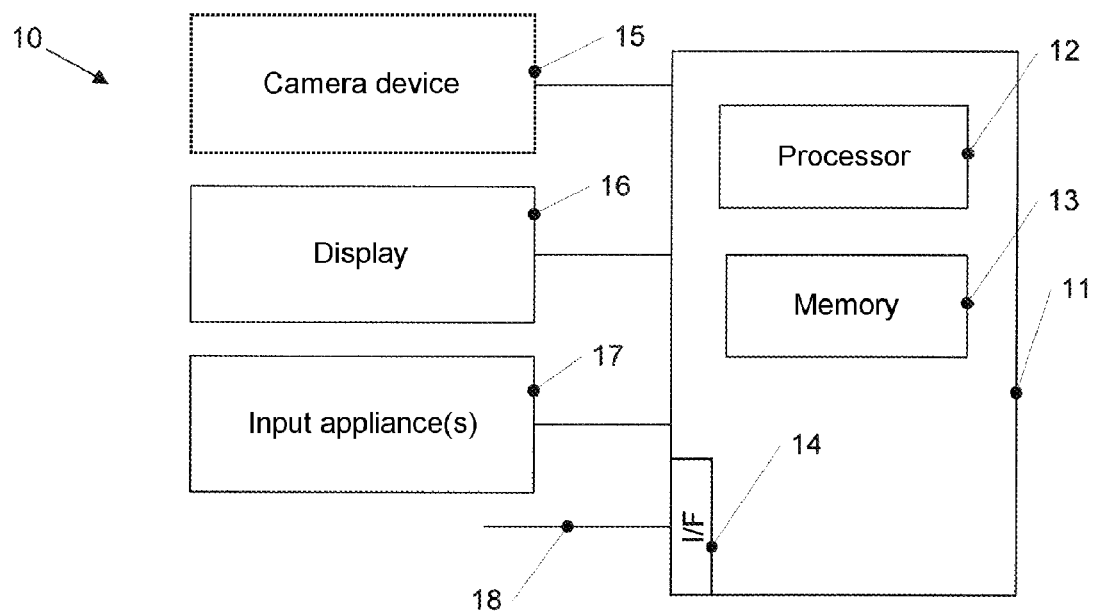
FIG. 1A shows an apparatus for virtual fitting of a pair of spectacles according to one exemplary embodiment.

FIG. 1A shows an exemplary embodiment of an apparatus for virtual fitting of a pair of spectacles according to one exemplary embodiment. The apparatus of FIG. 1A comprises a computing device 11, a processor 12 and a memory 13. The memory 13 serves to store data and, in the exemplary embodiment of FIG. 1A, comprises a random access memory (RAM), a read-only memory (ROM) and one or more mass storage media (hard disk, solid-state disk, optical drive, etc.). A program is saved in the memory 13, said program, when executed on the processor 12, carries out virtual fitting of a pair of spectacles as described above.

The apparatus of FIG. 1A further comprises a display 16 which displays a head of a person together with a spectacle frame when the computer program is executed on the processor 12. User inputs can be implemented by way of one or more input appliances 17, for example keyboard and mouse. Additionally or alternatively, the display 16 can be a touch-sensitive screen (touchscreen) in order to implement an input.

The apparatus of FIG. 1A furthermore comprises an interface 14 to a network 18, by means of which data can be received. In particular, this allows 3D models of spectacle frames with texture to be received. In some exemplary embodiments, data are also transmitted to a further computing device via the interface 14 in order to carry out calculations, such as the discussed calculations of metadata, on said further computing device.

In order to create a 3D model of a head of a person, to which the pair of spectacles should be fitted, the apparatus of FIG. 1A optionally comprises a camera device 15, by means of which a plurality of images of the person can be recorded from different directions; it being possible, as described, to determine the 3D model therefrom.

Figure 1B:
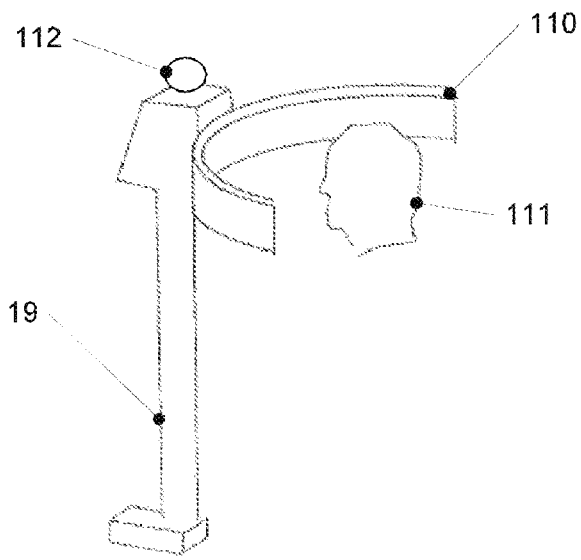
FIG. 1B shows an example of an implementation of a camera device of FIG. 1A.

FIG. 1B shows an exemplary embodiment for a camera device 15 of FIG. 1A. In the exemplary embodiment of FIG. 1B, a semicircular arrangement 110 of cameras is fastened to a column 19. A person can then position themselves in such a way that a head 111 of the person, as shown in FIG. 1B, is positioned in the semicircular arrangement 110 and can be recorded from different directions. From this, a 3D model of the head 111 can be created, as already explained above, wherein the texture of the model also arises from the image recordings. Moreover, the camera device of FIG. 1B comprises a panoramic camera 112 for the purposes of being able to ascertain an illumination during the image recording; this can then be used for an image synthesis, as described.

Figure 2:
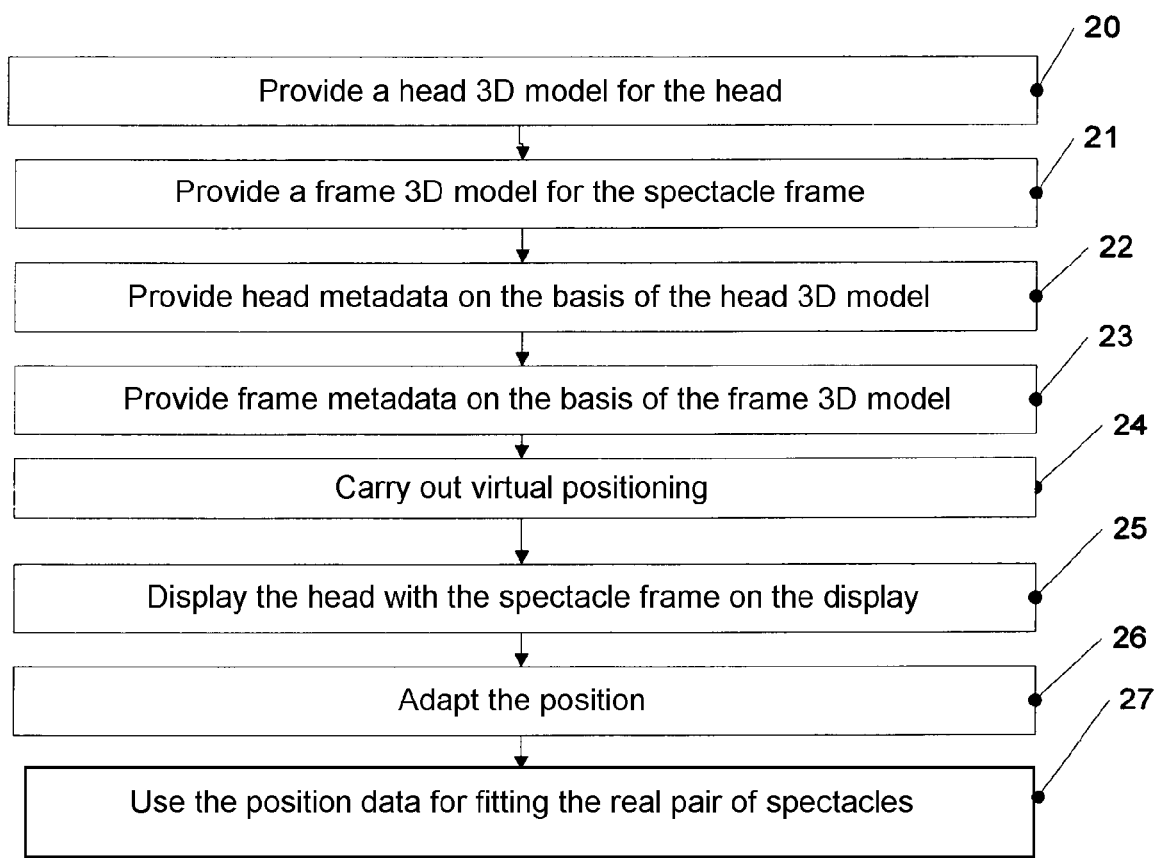
FIG. 2 shows a flowchart of a method according to one exemplary embodiment.

FIG. 2 shows a method according to one exemplary embodiment. A 3D model of a head of a user is provided in step 20 of FIG. 2, for example on the basis of camera recordings as described above, in particular using recordings of the camera device 15 of FIG. 1A. A frame 3D model for a spectacle frame to be fitted is provided in step 21, for example by a manufacturer.

Head metadata are provided on the basis of the head 3D model in step 22, as already described above, and frame metadata are provided on the basis of the frame 3D model in step 23, likewise as already described above. Steps 20 to 23 can also be carried out in a different sequence. Thus, step 22 and step 21 can be interchanged. The provision of the metadata in steps 22 and 23 can be implemented by newly calculating the metadata or by reading previously calculated metadata from a memory.

Here, the metadata can be calculated and provided as discussed above.

Then, the spectacle frame is positioned in virtual fashion in step 24, i.e., it is fitted to the head using the head metadata and the frame metadata. To this end, use is made of the already discussed methods. Thus, the virtual positioning comprises an approximate positioning on the basis of the head metadata and frame metadata and fine positioning on the basis of the 3D models of the head and of the spectacle frame.

Then, the head with the spectacle frame is presented on a display in step 25, on the display 16 in the case of the apparatus of FIG. 1A. This then allows the user to assess the look of the spectacle frame on the head.

Then, where necessary, the position of the spectacle frame can be displaced on the head in step 26 as described, for example, it can be displaced on the nose. This can be carried out by the user or else by an optician.

Optionally, use can then be made of fitting data, which describe the fitting of the pair of spectacles to the head, for the purposes of adapting a real pair of spectacles. By way of example, the earpieces of the real spectacle frame can be bent like during the virtual fitting of the model.

The method of FIG. 2 can be repeated for a plurality of spectacle frames in order to provide the user with an impression of the look of different spectacle frames. Then, the user can choose a spectacle frame on the basis of the presentations.

Various steps of the method in FIG. 2 are now explained in more detail with reference to FIGS. 3 to 10.

FIGS. 3A and 3C show an illustration for explaining a 3D model of the head. 31a denotes an example of a usable coordinate system, wherein the coordinate system—as explained above—is fixedly connected to the head, i.e., the coordinate system does not change its position and orientation relative to the head in the case of a rotation of the head. Here, FIG. 3A illustrates a 3D model 30 in the form of a triangle mesh with a plurality of vertices that are connected by edges. FIG. 3B shows a combination 31 of the triangle mesh and a texture. FIG. 3C shows a representation 32, as may be implemented on a screen on the basis of a model, in which only the texture is visible but not the individual vertices that are explicitly presented in FIGS. 3A and 3B for elucidation purposes. FIG. 4 shows a representation of the spectacle frame on the basis of the model, together with a coordinate system 41. The spectacle frame of 40 of FIG. 4 has a right spectacle earpiece 42A, a left spectacle earpiece 42B, a right hinge 43A, a left hinge 43B, a right frame rim 44A, a left frame rim 44B and a nose bridge 45

Figure 5:
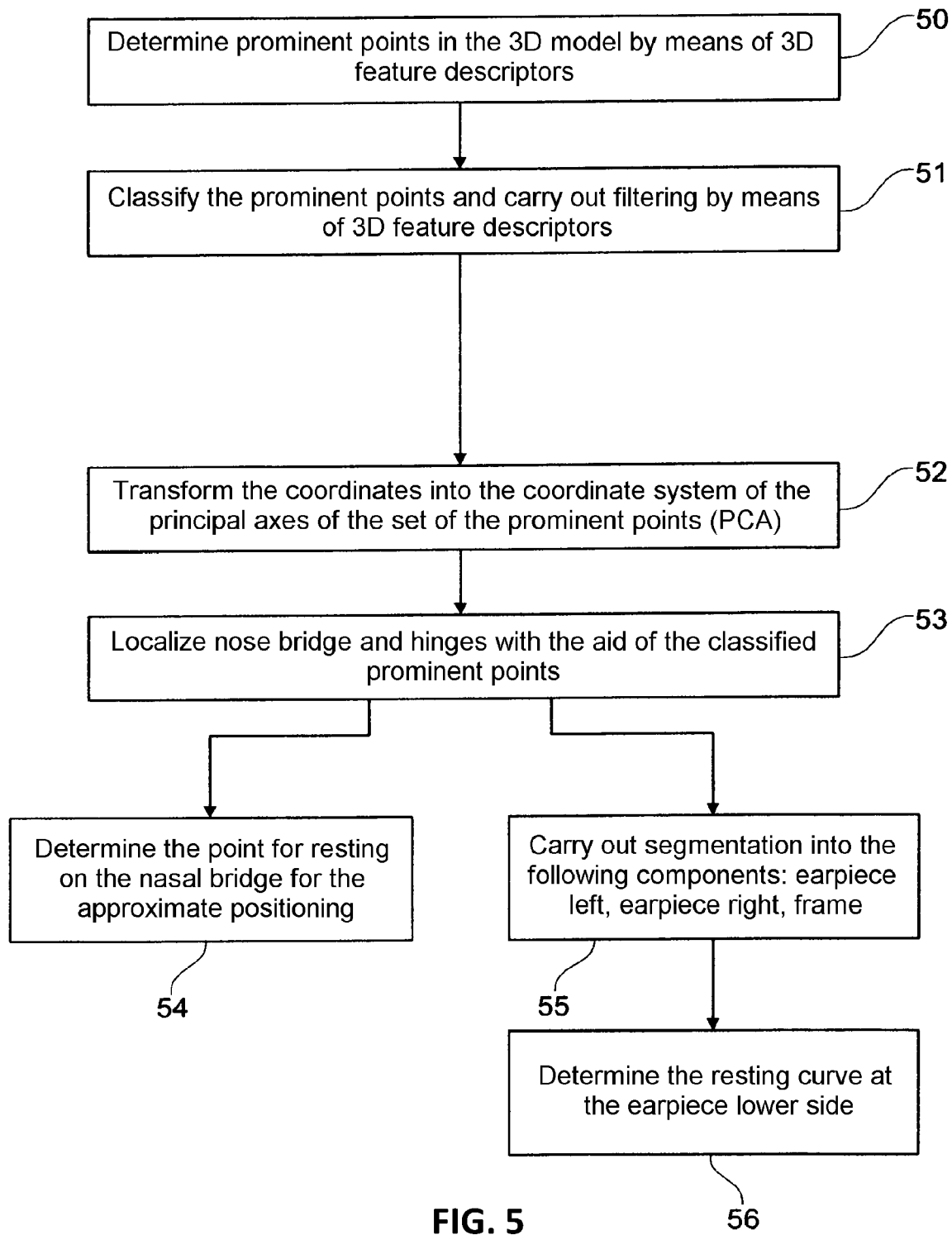
FIG. 5 shows a flowchart of a method for determining frame metadata according to one exemplary embodiment.
Figure 6A:
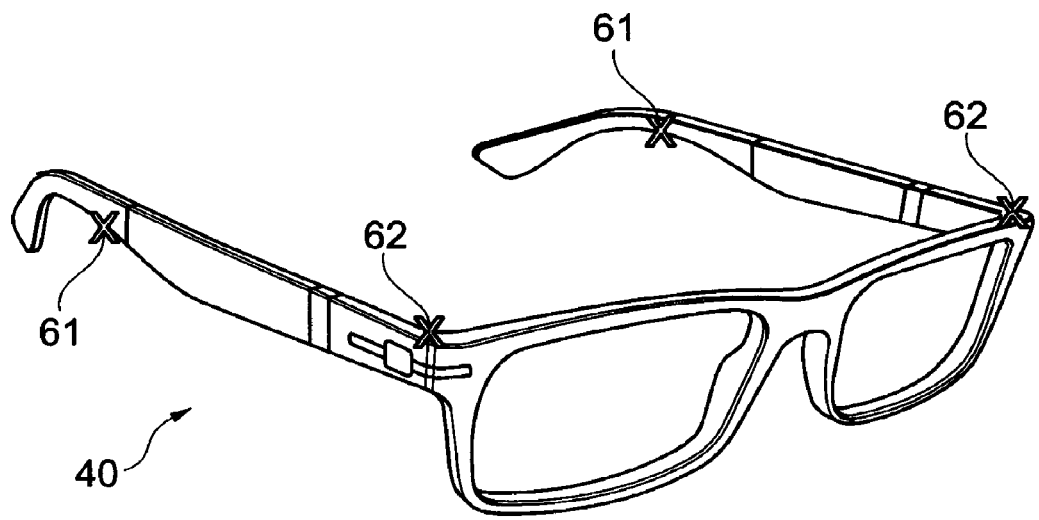
FIGS. 6A and 6B show illustrations for elucidating the manual determination of metadata.
Figure 6B:
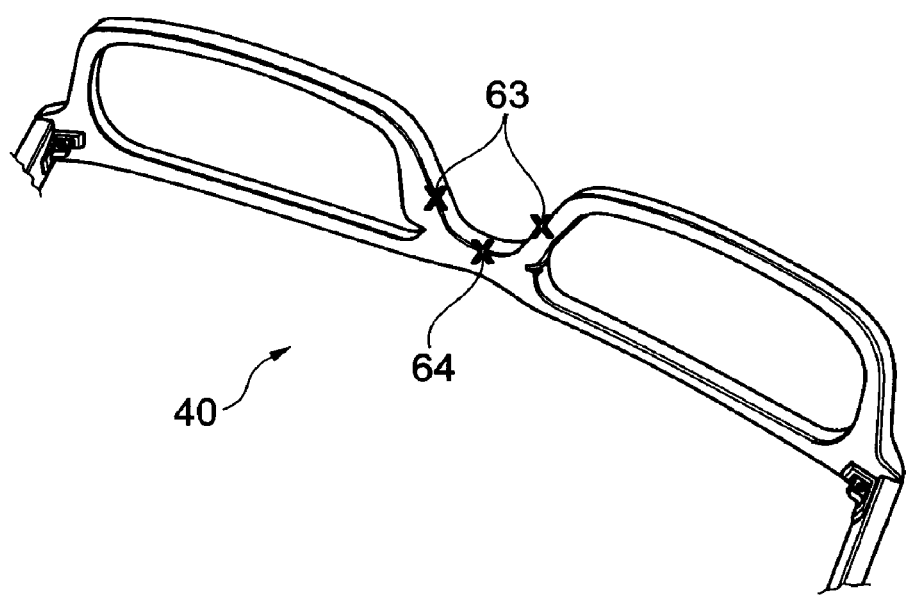

FIG. 5 shows a flowchart of a method for determining frame metadata, i.e., an example for implementing step 23 in FIG. 2. Prominent points in the 3D model of the frame are determined by means of 3D feature descriptors in step 50. These prominent points are classified and filtered in step 51. As an alternative to the determination by means of 3D feature descriptors, points can also be marked manually, as elucidated in FIGS. 6A and 6B. To this end, the spectacle frame 40, which was already described with reference to FIG. 4, is presented on a display and relevant points are marked. To this end, FIGS. 6A and 6B show ear resting points 61, hinge points 62, positions of nose pads 63 and a center point 64 of the nose bridge, which may serve as a resting point, as examples. It should be noted that the resting point need not lie directly on the spectacles but may also be spaced apart from the actual frame, particularly in the case of nose pads.

There is a coordinate transformation into the coordinate system of the principal axis of the prominent points classified in step 51 by a principal component analysis (PCA) in step 52 of FIG. 5 and nose bridge and hinges are localized in step 53 with the aid of the classified prominent points. Techniques to this end were likewise already described above.

Then, a point for resting on the nasal bridge is determined as a resting point in step 54 for the approximate positioning, as already described above. The 3D model of the spectacle frame is segmented into components (left spectacle earpiece, right spectacle earpiece and the remaining frame) in step 55 and a resting region at the earpiece lower side in the form of a resting curve is determined in step 56, as already described above.

Figure 7A:
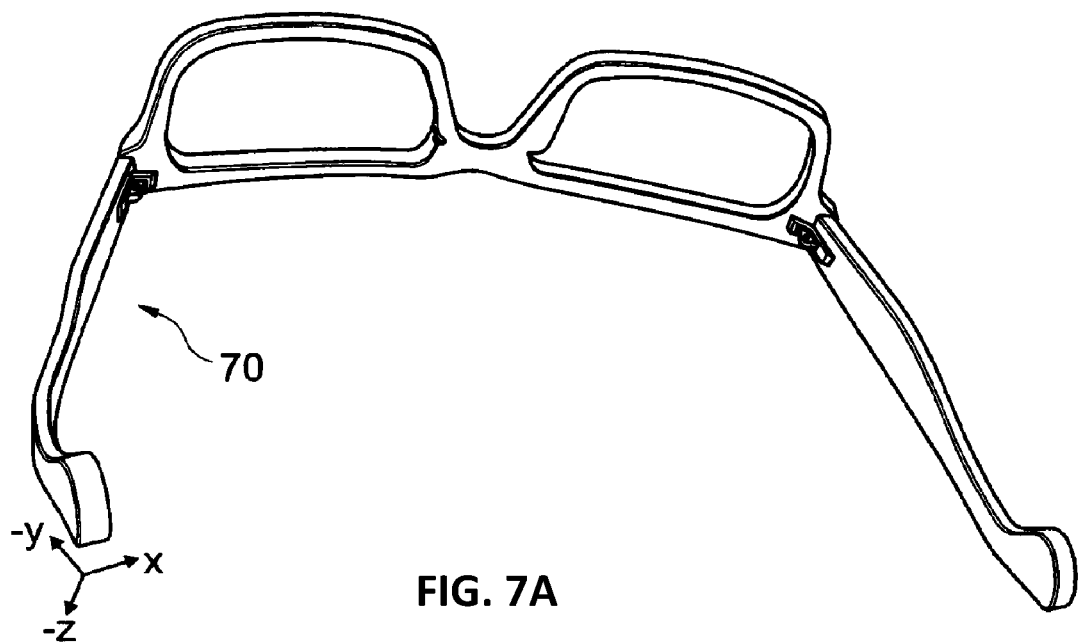
FIGS. 7A and 7B show illustrations of spectacle frames.
Figure 7B:
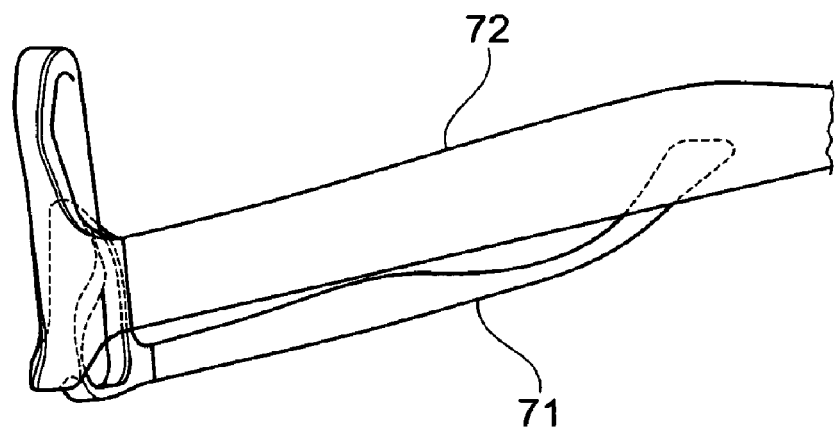

The earpiece lower side, on which the resting curve is determined, is presented for a spectacle frame 70 in FIG. 7A and for the spectacle earpieces 71 and 72 in a corresponding magnified view in FIG. 7B as a single point representation. Calculations need not be carried out with the aid of such a great number of points by using the resting region; the resting curve can be used instead.

Figure 8:
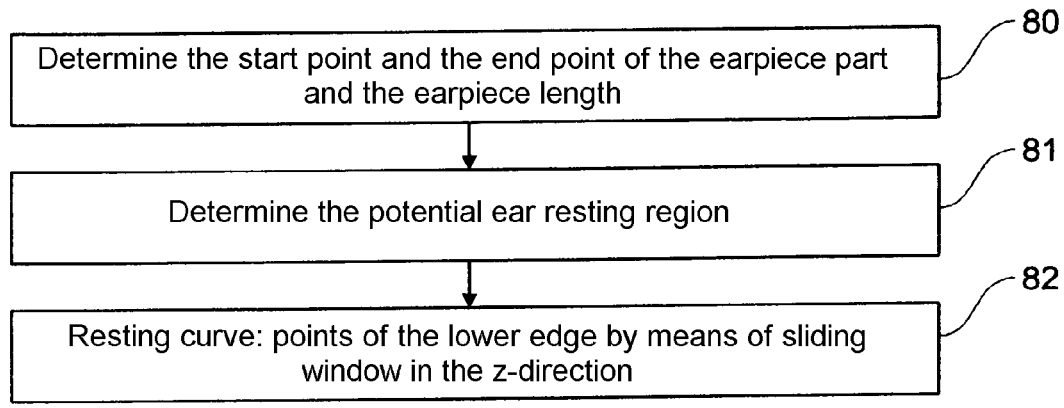
FIG. 8 shows a flowchart of a method for determining a resting curve.

FIG. 8 shows a flowchart of a method for determining the resting curve, i.e., a more detailed implementation of step 56 in FIG. 5. Start point and end point of the respective earpiece part (left spectacle earpiece or right spectacle earpiece) are described in step 80. Here, the method of FIG. 8 is carried out separately for the left spectacle earpiece and the right spectacle earpiece. A potential ear resting region is determined in step 81 and the resting curve is determined in step 82 by means of the "sliding window" technique described above. Here, steps 80 to 82 are carried out as already described in more detail above.

Figure 9:
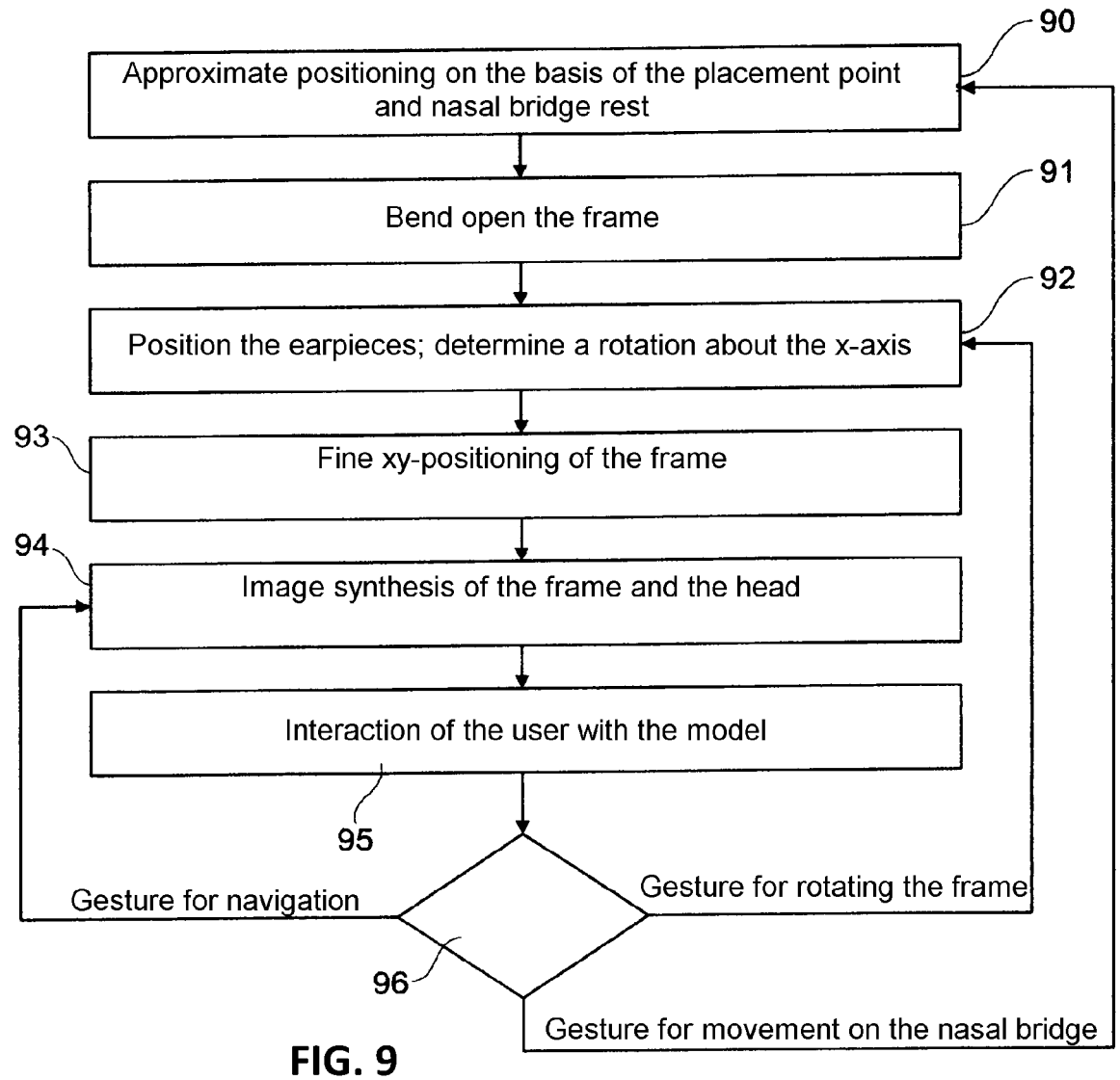
FIG. 9 shows a flowchart of a method for fitting a pair of spectacles.

FIG. 9 shows a flowchart of a method for virtual fitting and positioning of a spectacle frame on a head, wherein use is made of the models and metadata explained above. FIG. 9 represents an implementation example for steps 24 to 26 in FIG. 2.

There is approximate positioning in step 90 of FIG. 9, wherein the resting point of the metadata of the spectacle frame and the placement point of the metadata of the head are brought into correspondence. Then, the frame is bent open in step 91, wherein use is made here of the cylinder intersection methods already explained above. In the case of frames in which an inclination can be modified, i.e., the inclination can be modified by rotating the earpiece about the x-axis (the coordinate system 41 of FIG. 4 is used), this is implemented in step 92. Step 92 can be skipped in the case of spectacle frames where the frame metadata indicate that such a rotation is not possible.

Then, fine positioning of the frame in the xy-plane perpendicular to the z-direction is carried out in step 93, wherein the techniques already described above for the fine positioning are used here. Then, there is an image synthesis of the frame and of the head in step 94, corresponding to the positioning in steps 90 to 93, wherein, as explained above, light sources may be taken into account. Then, the user interacts with the represented model in step 95, i.e., the display of the frame and the head, using one or more input appliances (for example the input appliances 17 in FIG. 1A). As result of this, a navigation can be carried out, for example as indicated in step 96, i.e., the displayed model can be rotated, magnified or reduced in size. Then, step 94 is carried out again on the basis of these inputs; i.e., the image is redisplayed in accordance with the navigation. There may also be an input, also referred to as gesture, for rotating the frame, inter alia in order to compensate asymmetries in the face, as described above. In this case, the positioning is recalculated from step 92. Finally, the pair of spectacles can be moved up and down along the nasal bridge. This corresponds to a modification of the initial approximate positioning and hence the method is carried out again from step 90 in this case, wherein the newly set position on the nasal bridge is used as approximate positioning in step 90.

Figure 10A:
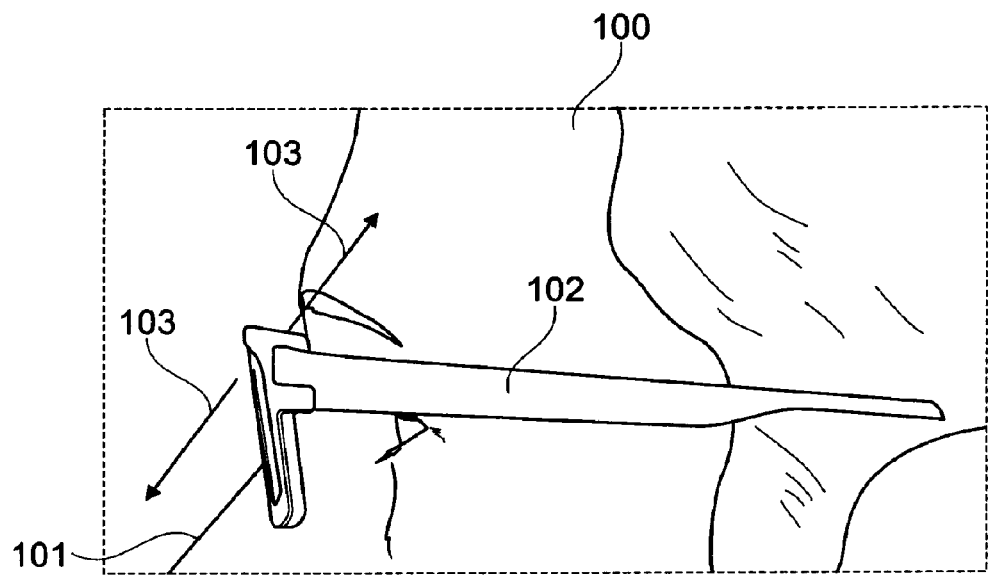
FIGS. 10A and 10B show illustrations for elucidating steps of the method of FIG. 9.
Figure 10B:
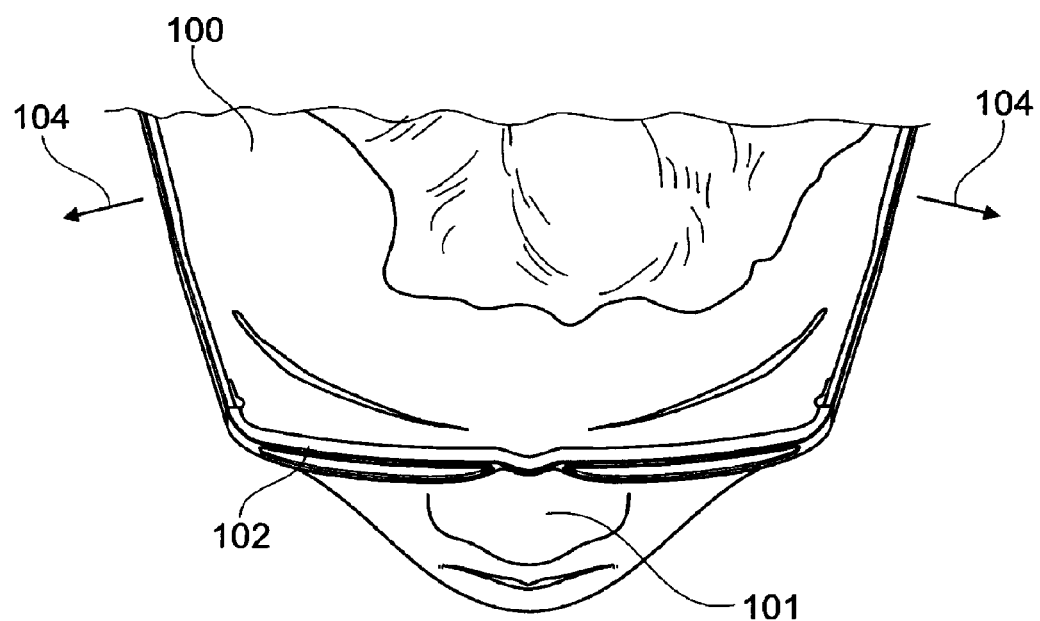

FIGS. 10A and 10B show representations of a head 100 together with a spectacle frame 102 for elucidating method steps of FIG. 9. FIG. 10A elucidates how the spectacle frame 102 can be displaced upward and downward along the nasal bridge 101 of the head 100 in accordance with arrows 103. This is an example of the movement on the nasal bridge according to step 96. FIG. 10B elucidates a bending open of the earpieces of the spectacle frame 102 in accordance with arrows 104, as carried out in step 91 of FIG. 9.

Figure 11:
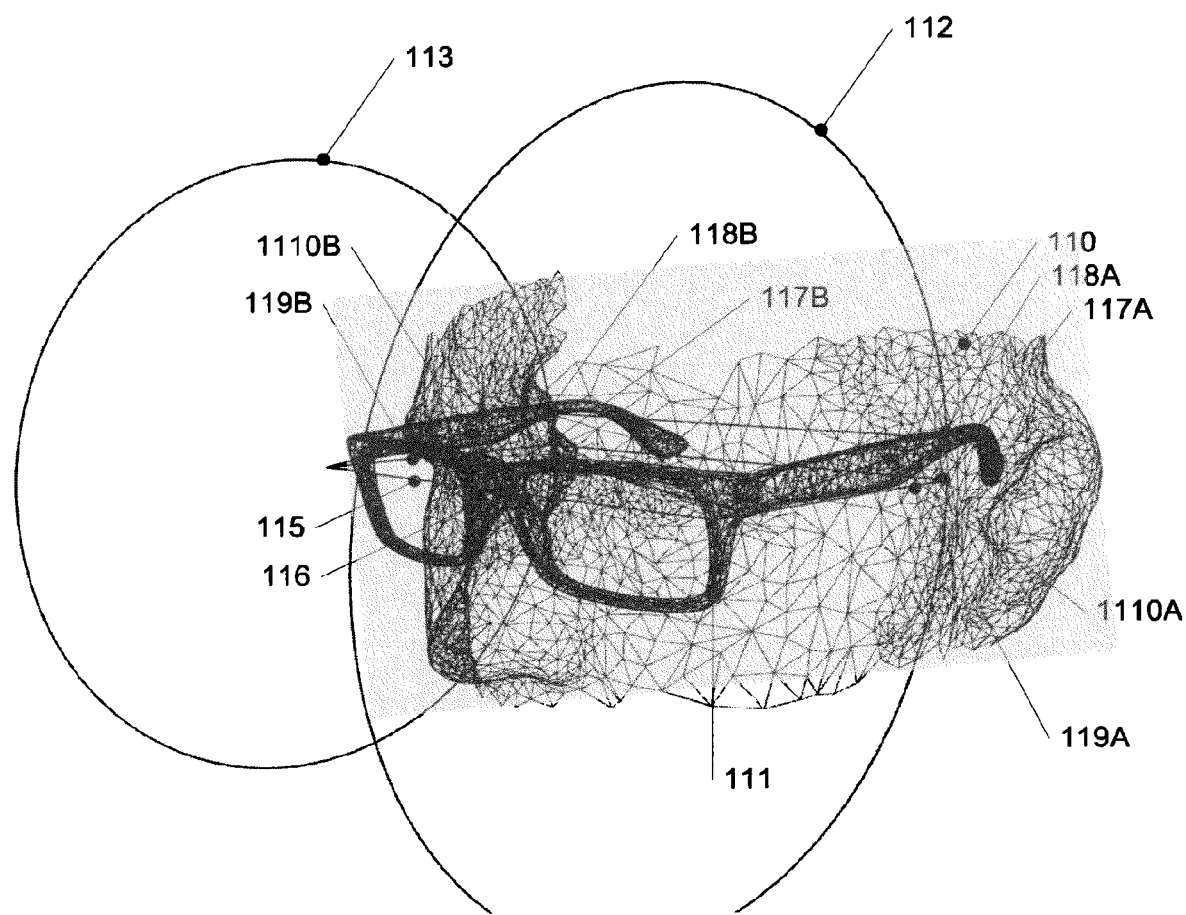
FIG. 11 shows an illustration for elucidating a rotation of the spectacle frame.

FIG. 11 shows an illustration for explaining the rotation of the frame about the x-axis by means of a cylinder intersection, as already explained above. FIG. 11 shows a 3D model of a head 110 and a 3D model of a spectacle frame 111, in each case as a 3D mesh. During the approximate positioning, the frame was initially positioned on the basis of a resting point 116. An axis 115 extends through the resting point 116 in the x-direction. A cylinder, indicated by circles 112, 113, has a radius to an ear resting point of the 3D model of the head 110. The point of intersection of the cylinder with a resting region of the spectacle frame, which is represented by the 3D model of the spectacle frame 111, with the cylinder yields a direction for the spectacle earpieces of the spectacle frame and consequently yields an angle through which the spectacle frame should be rotated about the axis 115. In the present case, a rotation is carried out from a position where the spectacle earpieces extend in the direction of lines 119A, 119B such that the spectacle earpieces now extend in the direction of the lines 1110A, 1110B.

Using the described methods and apparatuses, it is consequently possible to undertake virtual accurate fitting of a spectacle frame to a head, which then optionally, according to step 27 in FIG. 2, can also be used for fitting a real spectacle frame.

At least some possible exemplary embodiments are specified in the clauses below:

Clause 1. A computer-implemented method for virtual fitting of a pair of spectacles, comprising:
  i) fine virtual positioning of the spectacle frame on the basis of a 3D model (30, 31) of a head and a 3D model (40) of a spectacle frame,
  ii) characterized by
  iii) approximate virtual positioning of the spectacle frame on the head on the basis of head metadata for the 3D model (30, 31) of the head and frame metadata for the 3D model of the spectacle frame before the fine virtual positioning.

Clause 2. The method according to clause 1, characterized in that the frame metadata comprise first resting information items, which define one or more locations on the spectacle frame where the spectacle frame rests on the head, and/or the head metadata comprise second resting information items, which define one or more locations on the head where the spectacle frame rests on the head.

Clause 3. The method according to clause 2, characterized in that the first resting information items comprise a resting point associated with a nose bridge of the spectacle frame and wherein the second information items comprise a placement point associated with a nasal bridge of the 3D model of the head, and in that the approximate virtual positioning comprises a positioning where the resting point of the frame metadata is brought into correspondence with the placement point of the head metadata.

Clause 4. The method according to clause 3, characterized by calculating information items characterizing a nasal bridge of the head and determining the placement point on the basis of the information items characterizing the nasal bridge.

Clause 5. The method according to any one of clauses 1-4, characterized in that if a horizontal direction is defined corresponding to a connecting line of the eyes of the head when the head is held erect, if a vertical direction is defined as y-direction and if a direction perpendicular to the x- and y-direction is defined as z-direction, then a displacement of the spectacle frame in the z-direction is no more than 10% of a displacement of the spectacle frame in the x-y-direction during fine virtual positioning.

Clause 6. The method according to any one of clauses 1-5, characterized in that the method comprises at least one process from the group automatically determining at least one portion of the frame metadata and/or the head metadata manually determining at least one portion of the frame metadata and/or the head metadata.

Clause 7. The method according to clause 6, characterized in that the automatic determination comprises machine learning.

Clause 8. The method according to any one of clauses 1-7, characterized in that the method for providing the frame metadata comprises identifying prominent points in the 3D model of the spectacle frame and/or classifying prominent points in the 3D model of the spectacle frame.

Clause 9. The method according to clause 8, characterized in that the method further comprises an application of a coordinate transformation on the basis of the identified prominent points to at least one of the group of:
  the 3D model of the spectacle frame
  the identified prominent points
  the frame metadata.

Clause 10. The method according to any one of clauses 1-9, characterized in that the provision of the frame metadata comprises a segmentation of the 3D model of the spectacle frame into components of the spectacle frame, wherein the components preferably comprise at least one component of the group
  earpiece parts
  a remaining part of the spectacle frame apart from earpiece parts
  and/or
  wherein the head metadata comprise resting regions for the ears of the head, which regions are calculated on the basis of the segmented earpiece parts.

Clause 11. The method according to any one of clauses 1-10, characterized in that the frame metadata comprise bending information items about a flexibility of the spectacle frame and in that the virtual positioning comprises a bending of the spectacle frame on the basis of the information items about the flexibility.

Clause 12. The method according to any one of clauses 1-11, characterized in that the method comprises changing the position of the spectacle frame on the nose following the display, wherein an altered position of the spectacle frame on the nose is stored as a new placement point of the head metadata.

Clause 13. The method according to any one of clauses 1-12, characterized in that the method further comprises determining the 3D model of a head on the basis of image recordings and determining an ambient illumination when the images were recorded, and in that the display of the head with the frame positioned thereon comprises an image synthesis with a virtual illumination on the basis of the captured ambient illumination.

Clause 14. A computer program comprising a program code which, when executed on a processor, carries out the method according to any one of clauses 1-13.

Clause 15. An apparatus for virtual fitting of a pair of spectacles, comprising:
  a processor and
  a display,
  characterized by
  a computer program according to clause 14 to be executed on the processor.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents, and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A computer-implemented method for virtual fitting of a pair of spectacles, the method comprising:
   defining a horizontal direction corresponding to a connecting line between pupil centers of eyes of a head in a main fixation direction when the head is held erect as an x-direction, a vertical direction when the head is held erect as a y-direction, and a direction perpendicular to the x-direction and to the y-direction as a z-direction;
   performing an approximate virtual positioning of a spectacle frame on the head on a basis of head metadata for a 3D model of the head and frame metadata for a 3D model of the spectacle frame;
   subsequently performing a fine virtual positioning of the spectacle frame on the basis of the 3D model of the head and the 3D model of the spectacle frame;
   displacing, during the fine virtual positioning, the spectacle frame by a first distance perpendicular to the z-direction in a first displacement; and
   displacing, during the fine virtual positioning, the spectacle frame by a second distance along the z-direction in a second displacement,
   wherein the second distance is no more than 10% of the first distance,
   wherein the approximate positioning determines the position of the spectacle frame in the z-direction, and
   wherein the position of the spectacle frame in the z-direction remains fixed during the fine positioning.

2. The method as claimed in claim 1, wherein the approximate positioning determines the position of the spectacle frame in the z-direction.

3. The method as claimed in claim 1, wherein providing the frame metadata comprises at least one of identifying prominent points in the 3D model of the spectacle frame or classifying the prominent points in the 3D model of the spectacle frame.

4. The method as claimed in claim 3, further comprising:
   applying a coordinate transformation on the basis of the identified prominent points to at least one of the group of:
   the 3D model of the spectacle frame,
   the identified prominent points, or
   the frame metadata.

5. The method as claimed in claim 1, wherein at least one of the frame metadata includes first resting information items, which define one or more locations on the spectacle frame where the spectacle frame rests on the head, or
   the head metadata includes second resting information items, which define one or more locations on the head where the spectacle frame rests on the head.

6. The method as claimed in claim 5, wherein the first resting information items comprise a resting point associated with a nose bridge of the spectacle frame and wherein the second information items comprise a placement point associated with a nasal bridge of the 3D model of the head,
   wherein the approximate virtual positioning further comprises a positioning where the resting point of the frame metadata is brought into correspondence with the placement point of the head metadata.

7. The method as claimed in claim 6, further comprising:
   calculating an information item defining a nasal bridge of the head; and
   determining the placement point on the basis of the information item defining the nasal bridge,
   wherein the information item defining the nasal bridge is a 3D curve.

8. The method as claimed in claim 7, wherein the 3D curve has a parameterization, and wherein the parameterization is defined as a function of a coordinate of the y-direction.

9. The method as claimed in claim 1, further comprising at least one process from the group of:
   automatically determining at least one portion of the frame metadata and/or the head metadata; or
   manually determining at least one portion of the frame metadata and/or the head metadata.

10. The method as claimed in claim 9, wherein the automatic determination comprises machine learning.

11. The method as claimed in claim 1, wherein the frame metadata comprise bending information items about a flexibility of the spectacle frame, and wherein the virtual positioning comprises a bending of the spectacle frame on the basis of the information items about the flexibility.

12. The method as claimed in claim 1, further comprising:
   displaying the 3D model of the head with the spectacle frame positioned thereon; and
   changing a position of the displayed spectacle frame on the nose to an altered position,
   wherein the altered position of the spectacle frame on the nose is stored as a new placement point of the head metadata.

13. The method as claimed in claim 1, further comprising:
   recording images of the head to determine the 3D model of the head;
   capturing an ambient illumination when recording the images;
   performing an image synthesis with a virtual illumination on a basis of the captured ambient illumination; and
   displaying the 3D model of the head with the spectacle frame positioned thereon.

14. A computer program stored on a non-transitory computer storage medium and comprising a program code which, when executed on a processor, carries out the method as claimed in claim 1.

15. An apparatus for virtual fitting of a pair of spectacles, comprising:
   a processor;
   a display; and
   a computer program as claimed in claim 14 being stored on a non-transitory computer storage medium, the computer program being configured to be executed on the processor.

* * * * *

UNITED STATES PATENT AND TRADEMARK OFFICE
CERTIFICATE OF CORRECTION

PATENT NO.         : 11,215,845 B2
APPLICATION NO.    : 16/699590
DATED              : January 4, 2022
INVENTOR(S)        : Schwarz et al.

It is certified that error appears in the above-identified patent and that said Letters Patent is hereby corrected as shown below:

In the Specification

In Column 8, Lines 15 to 16, change "Nießner" to – Nießner –

In Column 11, Lines 26 to 27, change "Hauptkrummung" to – Hauptkrümmung –

In Column 12, Line 56, change "Uberwachtes" to – Überwachtes –

In Column 13, Line 20, change "Docs.opencv.org//3.1.0/dc/ddb/ml_intro.html" to
– Docs.opencv.org//3.1.0/dc/dd6/ml_intro.html –

In Column 16, Line 63, change "0=0.76." to – β=0.76. –

In Column 22, Line 26, change "$D_z^{-1}(Di\ (x1))$" to – $D_z^{-1}(D_z\ (x1))$ –

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*